US008437840B2

(12) United States Patent
Patel et al.

(10) Patent No.: US 8,437,840 B2
(45) Date of Patent: May 7, 2013

(54) EPISODE CLASSIFIER ALGORITHM

(75) Inventors: Amisha S. Patel, Maple Grove, MN (US); Bruce D. Gunderson, Plymouth, MN (US); Mark L. Brown, North Oaks, MN (US)

(73) Assignee: Medtronic, Inc., Minneapolis, MN (US)

(*) Notice: Subject to any disclaimer, the term of this patent is extended or adjusted under 35 U.S.C. 154(b) by 88 days.

(21) Appl. No.: 13/245,632

(22) Filed: Sep. 26, 2011

(65) Prior Publication Data

US 2013/0079651 A1    Mar. 28, 2013

(51) Int. Cl.
    *A61B 5/04*    (2006.01)
(52) U.S. Cl.
    USPC ............................................ 600/515; 607/14
(58) Field of Classification Search .................. 600/508, 600/509, 515–519; 607/14, 18
    See application file for complete search history.

(56) References Cited

U.S. PATENT DOCUMENTS

| | | |
|---|---|---|
| 4,140,131 A | 2/1979 | Dutcher et al. |
| 4,374,382 A | 2/1983 | Markowitz |
| 4,428,378 A | 1/1984 | Anderson et al. |
| 4,549,548 A | 10/1985 | Wittkampf et al. |
| 4,672,122 A | 6/1987 | Sommer et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,133,046 A | 7/1992 | Kaplan et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,193,550 A | 3/1993 | Duffin |
| 5,201,865 A | 4/1993 | Kuehn |
| 5,215,081 A | 6/1993 | Ostroff |
| 5,224,475 A | 7/1993 | Berg et al. |
| 5,226,415 A | 7/1993 | Girodo et al. |
| 5,251,626 A | 10/1993 | Nickolls et al. |
| 5,280,792 A | 1/1994 | Leong et al. |
| 5,292,343 A | 3/1994 | Blanchette et al. |

(Continued)

FOREIGN PATENT DOCUMENTS

| | | |
|---|---|---|
| WO | WO 03/094721 A1 | 11/2003 |
| WO | WO 2007/106455 A2 | 9/2007 |
| WO | WO 2007/117813 A2 | 10/2007 |
| WO | WO 2008/026166 A2 | 3/2008 |

OTHER PUBLICATIONS

U.S. Appl. No. 12/837,320, by Hendrikus A. Westendorp, filed Jul. 15, 2010.

(Continued)

*Primary Examiner* — Brian T Gedeon
(74) *Attorney, Agent, or Firm* — Michael C. Soldner

(57) ABSTRACT

The present disclosure is directed to the classification of cardiac episodes using an algorithm. In various examples, an episode classification algorithm evaluates electrogram signal data collected by an implantable medical device. The episode classification algorithm may classify may include a sinus template and a comparison of the electrogram signal to the sinus template. Possible classifications of the cardiac episode may include, for example, unknown, inappropriate, appropriate, supraventricular tachycardia, ventricular tachycardia, ventricular fibrillation or ventricular over-sensing.

22 Claims, 15 Drawing Sheets

U.S. PATENT DOCUMENTS

| | | | |
|---|---|---|---|
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,379,776 A | 1/1995 | Murphy et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,471,382 A | 11/1995 | Tallman et al. |
| 5,507,746 A | 4/1996 | Lin |
| 5,507,786 A | 4/1996 | Morgan et al. |
| 5,509,927 A | 4/1996 | Epstein et al. |
| 5,527,344 A | 6/1996 | Arzbaecher et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,594,638 A | 1/1997 | Iliff |
| 5,626,140 A | 5/1997 | Feldman et al. |
| 5,660,176 A | 8/1997 | Iliff |
| 5,660,183 A | 8/1997 | Chiang et al. |
| 5,707,398 A | 1/1998 | Lu |
| 5,722,997 A | 3/1998 | Nedungadi et al. |
| 5,722,999 A | 3/1998 | Snell |
| 5,730,141 A | 3/1998 | Fain et al. |
| 5,741,311 A | 4/1998 | McVenes et al. |
| 5,755,735 A | 5/1998 | Richter et al. |
| 5,755,736 A | 5/1998 | Gillberg et al. |
| 5,755,739 A | 5/1998 | Sun et al. |
| 5,755,742 A | 5/1998 | Schuelke et al. |
| 5,776,168 A | 7/1998 | Gunderson |
| 5,814,088 A | 9/1998 | Paul et al. |
| 5,817,137 A | 10/1998 | Kaemmerer |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,910,156 A | 6/1999 | Cinbis et al. |
| 5,944,746 A | 8/1999 | Kroll |
| 6,056,690 A | 5/2000 | Roberts |
| 6,067,473 A | 5/2000 | Greeninger et al. |
| 6,070,097 A | 5/2000 | Kreger et al. |
| 6,085,118 A | 7/2000 | Hirschberg et al. |
| 6,090,044 A | 7/2000 | Bishop et al. |
| 6,112,119 A | 8/2000 | Schuelke et al. |
| 6,126,595 A | 10/2000 | Amano et al. |
| 6,129,745 A | 10/2000 | Sun et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,192,273 B1 | 2/2001 | Igel et al. |
| 6,203,495 B1 | 3/2001 | Bardy |
| 6,221,011 B1 | 4/2001 | Bardy |
| 6,261,230 B1 | 7/2001 | Bardy |
| 6,266,554 B1 | 7/2001 | Hsu et al. |
| 6,270,457 B1 | 8/2001 | Bardy |
| 6,280,380 B1 | 8/2001 | Bardy |
| 6,312,378 B1 | 11/2001 | Bardy |
| 6,315,719 B1 | 11/2001 | Rode et al. |
| 6,317,632 B1 | 11/2001 | Krig et al. |
| 6,317,633 B1 | 11/2001 | Jorgenson et al. |
| 6,336,903 B1 | 1/2002 | Bardy |
| 6,358,203 B2 | 3/2002 | Bardy |
| 6,368,284 B1 | 4/2002 | Bardy |
| 6,393,316 B1 | 5/2002 | Gillberg et al. |
| 6,398,728 B1 | 6/2002 | Bardy |
| 6,411,840 B1 | 6/2002 | Bardy |
| 6,434,428 B1 | 8/2002 | Sloman et al. |
| 6,440,066 B1 | 8/2002 | Bardy |
| 6,445,952 B1 | 9/2002 | Manrodt et al. |
| 6,449,508 B1 | 9/2002 | Sheldon et al. |
| 6,470,210 B1 | 10/2002 | Chen et al. |
| 6,477,417 B1 | 11/2002 | Levine |
| 6,493,586 B1 | 12/2002 | Stahmann et al. |
| 6,599,250 B2 | 7/2003 | Webb et al. |
| 6,607,485 B2 | 8/2003 | Bardy |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,669,631 B2 | 12/2003 | Norris et al. |
| 6,687,685 B1 | 2/2004 | Sadeghi et al. |
| 6,721,600 B2 | 4/2004 | Jorgenson et al. |
| 6,725,208 B1 | 4/2004 | Hartman et al. |
| 6,748,269 B2 | 6/2004 | Thompson et al. |
| 6,760,624 B2 | 7/2004 | Anderson et al. |
| 6,788,971 B1 | 9/2004 | Sloman et al. |
| 6,865,141 B2 | 3/2005 | Tada et al. |
| 6,974,413 B2 | 12/2005 | Bardy |
| 6,980,860 B2 | 12/2005 | Stadler et al. |
| 7,020,521 B1 | 3/2006 | Brewer et al. |
| 7,047,083 B2 | 5/2006 | Gunderson et al. |
| 7,069,085 B2 | 6/2006 | Cao et al. |
| 7,103,404 B2 * | 9/2006 | Stadler et al. ............ 600/515 |
| 7,115,095 B2 | 10/2006 | Eigler et al. |
| 7,167,747 B2 | 1/2007 | Gunderson et al. |
| 7,184,837 B2 | 2/2007 | Goetz |
| 7,206,633 B2 | 4/2007 | Saba |
| 7,212,849 B2 | 5/2007 | Zhang et al. |
| 7,236,828 B2 | 6/2007 | Casavant et al. |
| 7,266,409 B2 | 9/2007 | Gunderson |
| 7,280,869 B2 * | 10/2007 | Warman et al. ............ 607/14 |
| 7,286,997 B2 | 10/2007 | Spector et al. |
| 7,289,851 B2 | 10/2007 | Gunderson et al. |
| 7,308,309 B1 | 12/2007 | Koh |
| 7,314,451 B2 | 1/2008 | Halperin et al. |
| 7,333,855 B2 | 2/2008 | Gunderson et al. |
| 7,353,063 B2 | 4/2008 | Simms, Jr. |
| 7,369,893 B2 | 5/2008 | Gunderson |
| 7,396,330 B2 | 7/2008 | Banet et al. |
| 7,429,243 B2 | 9/2008 | KenKnight et al. |
| 7,430,446 B2 | 9/2008 | Li |
| 7,430,475 B2 | 9/2008 | Imoto et al. |
| 7,479,107 B2 | 1/2009 | Zhu et al. |
| 7,480,528 B2 | 1/2009 | Brockway et al. |
| 7,480,529 B2 | 1/2009 | Li |
| 7,490,085 B2 | 2/2009 | Walker et al. |
| 7,539,540 B2 | 5/2009 | Gunderson et al. |
| 7,567,835 B2 | 7/2009 | Gunderson et al. |
| 7,582,061 B2 | 9/2009 | Li et al. |
| 7,738,950 B2 | 6/2010 | Johnson et al. |
| 7,894,883 B2 | 2/2011 | Gunderson et al. |
| 7,974,690 B2 | 7/2011 | Kracker |
| 2001/0007053 A1 | 7/2001 | Bardy |
| 2001/0023419 A1 | 9/2001 | LaPointe et al. |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0036683 A1 | 2/2003 | Kehr et al. |
| 2003/0050563 A1 | 3/2003 | Suribhotla et al. |
| 2003/0065535 A1 | 4/2003 | Karlov et al. |
| 2003/0074026 A1 | 4/2003 | Thompson et al. |
| 2003/0204215 A1 | 10/2003 | Gunderson et al. |
| 2003/0216654 A1 | 11/2003 | Xu et al. |
| 2004/0015197 A1 | 1/2004 | Gunderson |
| 2004/0064161 A1 | 4/2004 | Gunderson et al. |
| 2004/0088018 A1 | 5/2004 | Sawchuk et al. |
| 2004/0093240 A1 | 5/2004 | Shah |
| 2004/0106955 A1 | 6/2004 | Swerdlow et al. |
| 2004/0122487 A1 | 6/2004 | Hatlestad et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0022181 A1 | 1/2005 | Fox et al. |
| 2005/0049910 A1 | 3/2005 | Lancaster et al. |
| 2005/0055166 A1 | 3/2005 | Miyano et al. |
| 2005/0060193 A1 | 3/2005 | Lancaster et al. |
| 2005/0065569 A1 | 3/2005 | Ricci et al. |
| 2005/0075902 A1 | 4/2005 | Wager et al. |

| | | |
|---|---|---|
| 2005/0080347 A1 | 4/2005 | Sheth et al. |
| 2005/0119534 A1 | 6/2005 | Trost et al. |
| 2005/0137636 A1 | 6/2005 | Gunderson et al. |
| 2005/0154421 A1 | 7/2005 | Ousdigian |
| 2005/0159785 A1 | 7/2005 | Rueter |
| 2005/0192506 A1 | 9/2005 | Kim et al. |
| 2005/0192836 A1 | 9/2005 | Rossinni et al. |
| 2005/0192844 A1 | 9/2005 | Esler et al. |
| 2006/0030890 A1 | 2/2006 | Cosentino et al. |
| 2006/0064020 A1 | 3/2006 | Burnes et al. |
| 2006/0064323 A1 | 3/2006 | Alleckson et al. |
| 2006/0074331 A1 | 4/2006 | Kim et al. |
| 2006/0074454 A1 | 4/2006 | Freeberg |
| 2006/0074464 A1 | 4/2006 | Subera et al. |
| 2006/0116732 A1 | 6/2006 | Gunderson et al. |
| 2006/0116733 A1 | 6/2006 | Gunderson et al. |
| 2006/0217621 A1 | 9/2006 | Kim et al. |
| 2006/0217769 A1 | 9/2006 | Saba |
| 2006/0235476 A1 | 10/2006 | Gunderson et al. |
| 2006/0241510 A1 | 10/2006 | Halperin et al. |
| 2006/0281998 A1 | 12/2006 | Li |
| 2007/0061393 A1 | 3/2007 | Moore |
| 2007/0100667 A1 | 5/2007 | Bardy |
| 2007/0123788 A1 | 5/2007 | Gunderson et al. |
| 2007/0123789 A1 | 5/2007 | Gunderson et al. |
| 2007/0123790 A1 | 5/2007 | Gunderson et al. |
| 2007/0123941 A1 | 5/2007 | Gunderson et al. |
| 2007/0135863 A1 | 6/2007 | Gunderson et al. |
| 2007/0135864 A1 | 6/2007 | Gunderson et al. |
| 2007/0167986 A1 | 7/2007 | Gunderson et al. |
| 2007/0203415 A1 | 8/2007 | Bardy |
| 2007/0239043 A1 | 10/2007 | Patel et al. |
| 2008/0045815 A1 | 2/2008 | Derchak et al. |
| 2008/0082012 A1 | 4/2008 | Gunderson et al. |
| 2008/0132965 A1 | 6/2008 | Ostroff et al. |
| 2008/0161872 A1 | 7/2008 | Gunderson |
| 2008/0162393 A1 | 7/2008 | Iliff |
| 2008/0172098 A1 | 7/2008 | Gunderson |
| 2008/0269625 A1 | 10/2008 | Halperin et al. |
| 2008/0275349 A1 | 11/2008 | Halperin et al. |
| 2008/0312541 A1 | 12/2008 | Lewicke et al. |
| 2009/0030292 A1 | 1/2009 | Bartnik et al. |
| 2009/0036757 A1 | 2/2009 | Brockway et al. |
| 2009/0054741 A1 | 2/2009 | McAleer |
| 2009/0076844 A1 | 3/2009 | Koegen |
| 2009/0076845 A1 | 3/2009 | Bellin et al. |
| 2009/0222054 A1 | 9/2009 | Kim et al. |
| 2010/0280567 A1 | 11/2010 | Gunderson |
| 2011/0098766 A1 | 4/2011 | Gunderson |
| 2011/0112417 A1 | 5/2011 | Gunderson et al. |

OTHER PUBLICATIONS

U.S. Appl. No. 13/245,585, by Amisha S. Patel, filed Sep. 26, 2011.
Herskovits et al., "Algorithms for Bayesian Belief-Network Precomputation," Methods of Information in Medicine, vol. 30, 1991, pp. 81-89.
Grunkmeier et al., "Bayesian Analysis: A New Statistical Paradigm for New Technology," The Annals of Thoracic Surgery, vol. 74, No. 6, pp. 1901-1908, Dec. 2002.
Gao et al., "Arrthymia Identification from ECG Signals with a Neural Network Classifier Based on a Bayesian Framework," 24th SGAI International Conference on Innovative Techniques and Applications of Artificial Intelligence, Cambridge, UK, Dec. 13, 2004, 12 pp.
Charniak, "Bayesian Networks Without Tears," AI Magazine, Winter 1991, 14 pp.
U.S. Appl. No. 11/564,135, by Bruce D. Gunderson, filed Nov. 28, 2006.
U.S. Appl. No. 11/278,001, by Amisha S. Patel, filed Mar. 30, 2006.

* cited by examiner

EPISODE CLASSIFIER ALGORITHM

TECHNICAL FIELD

The invention relates to an algorithm for classifying cardiac episodes detected by an implantable medical device (IMD).

BACKGROUND

Some implantable medical devices (IMDs) monitor physiological parameters or signals of the patients within which they are implanted. Such implantable medical devices may detect episodes based on the monitoring. An IMD may store a variety of data regarding detected episodes, and a clinician may retrieve the episode data from the IMD for diagnosing the patient and/or confirming the accuracy of the detection of the episodes by the IMD. For example, implantable cardioverter-defibrillators (ICDs) may detect cardiac episodes, such as tachyarrhythmia episodes, based on monitoring cardiac electrogram signals and, in some cases, additional physiological signals or parameters. A clinician may review the data stored by the ICD for the episodes to confirm that accuracy of the diagnosis of tachyarrhythmia by the ICD.

As the memory capacity and diagnostic capabilities of IMDs, such as ICDs, increases, the amount of time required to adequately review the retrieved data to determine whether the detection of episodes and delivery of therapy by the device was appropriate also increases. Manual review of episodes may be challenging because of the number of patients a clinician follows, an increase in the total number of episodes to review and the significant level of expertise required. Additionally, the time available for clinicians with expertise to review each episode has been reduced. This may result in a reduction in the quality of management of those patients having implanted devices.

Automated algorithms for post-processing cardiac episodes previously detected by ICDs have been proposed to address these concerns. Such algorithms generally evaluate the cardiac electrogram and other data stored by an ICD for an episode to provide an independent classification of the episode. The post-processing classification may be compared to the classification made by the ICD to determine the accuracy of the classification by the ICD. Such algorithms may potentially suggest ICD parameter changes and/or changes to medical therapy, such as changes in medication, therapy delivery, use of ablation procedures, etc. One algorithm for automated algorithms for post-processing of cardiac episodes is disclosed in U.S. Pat. No. 7,894,883 to Gunderson et al., which is incorporated herein by reference in its entirety.

SUMMARY

In general, the disclosure describes techniques for improving episode classification during post-processing. In various examples consistent with the present disclosure, an episode classification algorithm may include, for example, a sinus template and a template matching algorithm.

In one example, a method comprises collecting a sinus template from a first ventricular EGM signal, wherein the sinus template comprises a portion of the first ventricular EGM signal including at least one ventricular beat, and wherein collecting the sinus template comprises collecting the sinus template from a portion of the ventricular EGM that occurred when the ventricular EGM signal and an atrial EGM signal indicated a one to one ratio of atrial events to ventricular events, a P-R interval greater than a first predetermined threshold, an R-R interval greater than a second predetermined threshold, and two consecutive R-R intervals within a predetermined range. The method further includes comparing the sinus template to a second ventricular EGM signal, and determining, based on the comparison, whether the morphology of the second ventricular EGM signal matches the sinus template.

In another example, the disclosure is directed to a processor configured to collect a sinus template from a first ventricular EGM signal, wherein the sinus template comprises a portion of the first ventricular EGM signal including at least one ventricular beat, and wherein collecting the sinus template comprises collecting the sinus template from a portion of the ventricular EGM that occurred when the ventricular EGM signal and an atrial EGM signal indicated a one to one ratio of atrial events to ventricular events, a P-R interval greater than a first predetermined threshold, an R-R interval greater than a second predetermined threshold; and two consecutive R-R intervals within a predetermined range. The processor is further configured to compare the sinus template to a second ventricular EGM signal, and determine, based on the comparison, whether the morphology of the second ventricular EGM signal matches the sinus template.

In another example, the disclosure is directed to a device comprising means for collecting a sinus template from an EGM signal; the sinus template collected when the EGM signal has a one to one ratio of atrial events to ventricular events, a P-R interval greater than 80 milliseconds (ms), an R-R interval greater than 500 ms; and two consecutive R-R intervals within 50 ms of each other; means for comparing the sinus ventricular beat template to a second EGM signal, and means for determining, based on the comparison, whether the morphology of the second EGM signal matches the sinus template.

In another embodiment, the invention is directed to a computer-readable medium containing instructions. The instructions cause a programmable processor to collect a sinus template from a first ventricular EGM signal, wherein the sinus template comprises a portion of the first ventricular EGM signal including at least one ventricular beat, and wherein collecting the sinus template comprises collecting the sinus template from a portion of the ventricular EGM that occurred when the ventricular EGM signal and an atrial EGM signal indicated a one to one ratio of atrial events to ventricular events, a P-R interval greater than a first predetermined threshold, an R-R interval greater than a second predetermined threshold; and two consecutive R-R intervals within a predetermined range, compare the sinus template to a second ventricular EGM signal, and determine, based on the comparison, whether the morphology of the second ventricular EGM signal matches the sinus template.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
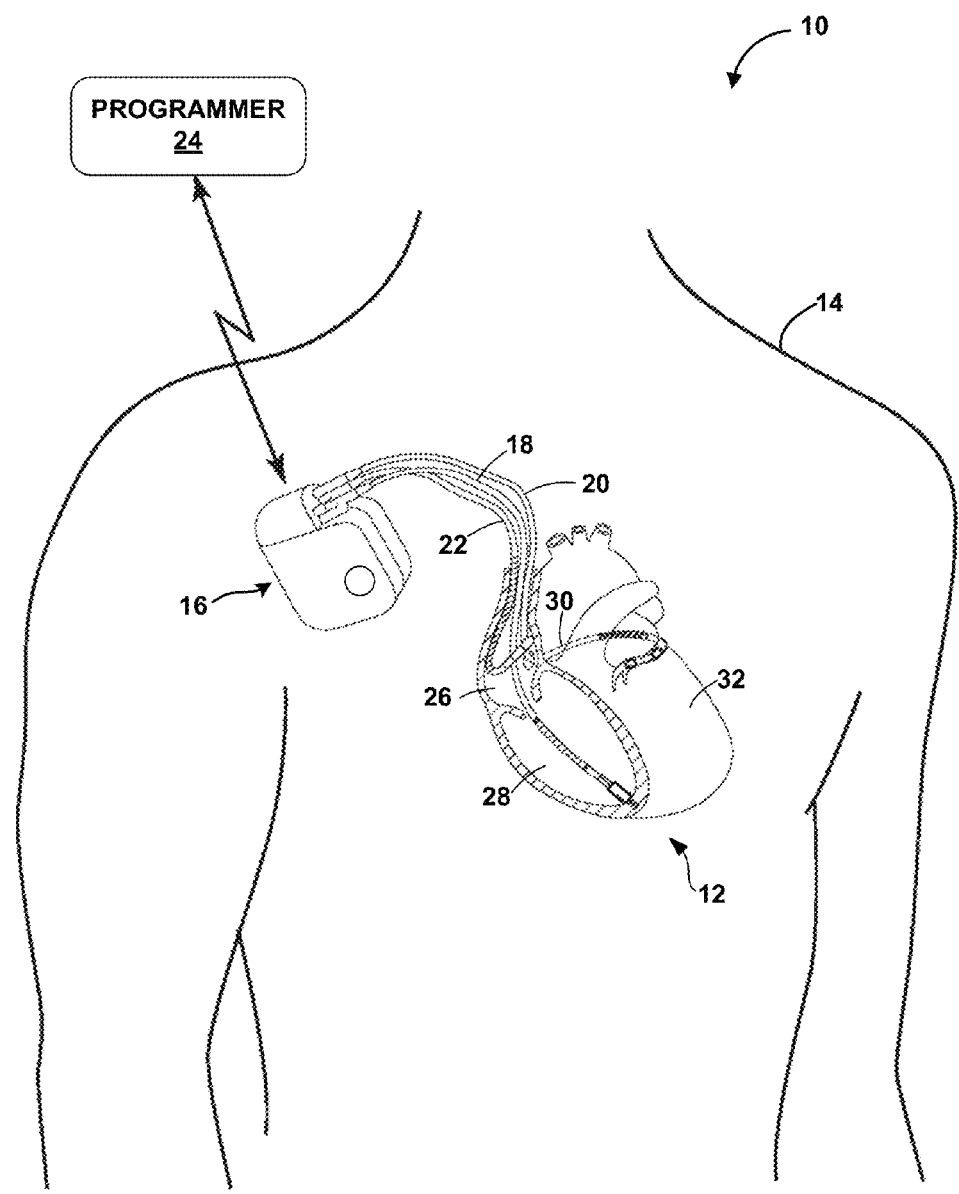
FIG. 1 is a conceptual diagram illustrating an example system for classifying a cardiac episode consistent with an example of the present disclosure.

This disclosure describes techniques for classifying cardiac episodes. In particular, the disclosure is describes techniques for an external device to evaluate a prior classification of an episode by an implantable medical device (IMD). The techniques described below may be used alone or in combination.

In general, an IMD transmits electrogram (EGM) signal data or other data associated with a cardiac episode diagnosed by the IMD to an external computing device. In some examples the data is transmitted after the episode is over. In some examples, the data is transmitted at predetermined intervals. The data stored by an IMD for a cardiac episode diagnosed by the IMD may include the diagnosis made by the IMD and data leading up to diagnosis of the particular cardiac episode. In some examples, IMD may include episodes resulting in either anti-tachycardia pacing or a shock in response to a diagnosis of either ventricular tachycardia or ventricular fibrillation. It is also possible that the IMD may have misdiagnosed a supraventricular tachycardia (SVT), such as sinus tachycardia or an atrial arrhythmia, or noise as a treatable, i.e., shockable, episode.

In some examples, an external computing device analyzes the EGM signal that was previously used by the IMD to classify an episode, and generates its own classification of the episode based on the EGM signal. In some examples, the external device determines whether the classification of the episode by the IMD was correct by comparing its classification of the episode to that of the IMD. The techniques described below may reduce the number of episodes that the external device is unable to classify with a reasonable degree of confidence.

In some examples, a post-processing classification algorithm may reduce the number of EGM episodes that are unable to be classified confidently by classifying an single episode based on information from both a near-field (NF) EGM channel and a far-field (FF) EGM channel. The use of both the NF and FF channels allows for classification even in instances where one or the other channel would result in an unknown classification. This more robust classification system compensates for over- or under-sensing or other sensing problems that may occur on one of the two channels. Consistent with the present disclosure, the FF EGM channel is given priority assuming that the episode on the FF EGM channel is not classified as unknown by the algorithm. Additionally, in some examples where an episode is determined to include ventricular over-sensing (VOS) on either channel, then the final classification is ventricular over-sensing, regardless of which channel is categorized as ventricular over-sensing.

A post-processing classification algorithm using both a NF EGM channel and A FF EGM channel may be different in certain respects for each channel. For example, different thresholds may be used on the NF and FF channel. In addition, when comparing a channel signal to a template, the template may be specific to the channel.

In some examples, a post-processing classification algorithm may additionally or alternatively reduce the number of unknown EGM episode by using a sinus tachycardia template. A sinus tachycardia template, referred to herein as a sinus template, is a template comprising one or more ventricular or atrial beats, e.g., including one or more R-waves or P-waves, derived from ventricular electrogram data including one or more beats during sinus rhythm. In some examples, an atrial template may be used to discriminate true P-waves from far-field R-waves detected incorrectly by an IMD as P-waves.

Either an IMD device or an external device may capture a sinus template automatically based on a variety of characteristics. A sinus template may be automatically selected by an IMD or an external device based on a number of factors which would lead to a conclusion that the cardiac rhythm underlying the candidate ventricular EGM data is a sinus tachycardia, including a rhythm with a 1:1 ratio of atrial sensed ($A_s$) events to ventricular sensed ($V_s$) events, a PR (P-wave to R-wave) interval of greater than 80 milliseconds (ms), an RR (R-wave to R-wave) interval greater than 500 ms, and two consecutive RR interval values within less than 50 ms of each other. The template may be selected either from a post ATP rhythm or from a pre-diagnosis rhythm, assuming the appropriate criteria are met.

A sinus template may also be selected from an episode that has been classified either by an IMD or an external computing device as supraventricular tachycardia. A ventricular beat leading up to diagnosis as SVT is selected and stored as a template. In some examples, templates may be stored for each channel providing an EGM signal. The templates may then be compared to EGM signals from the same respective channel.

The sinus template may be used by a post-processing algorithm to determine whether the morphology of the beats within an episode corresponds to the sinus template. If the morphologies match, the episode is classified as supraventricular tachycardia (SVT). In some examples, a different sinus template may be compared to beats for each of a plurality of EGM signals associated with a particular cardiac episode. Such a classification of an episode received from IMD by an external post-processing algorithm may indicate a misdiagnosis by the IMD.

A sinus template may also be used by an IMD for real-time detection decisions. In some examples, a sinus template is used either to strengthen or make a detection decision within an IMD. If the current ventricular rate places the rhythm within the VT/VF zone, a current ventricular EGM beat morphology is compared to the sinus template. If the current beat morphology and the sinus template match, then the IMD withholds detection of VT/VF. If the two do not match, then IMD continues with a VT/VF detection algorithm.

The present disclosure also includes an example method of classifying an episode when a 1:1 ratio of atrial sensed events to ventricular sensed events is present. The method of classification may be used by an IMD in real time to diagnosis a cardiac event, or by an external computing device to evaluate the diagnosis of an event by the IMD. When a 1:1 ratio of atrial sensed events to ventricular sensed events is present, a determination may be made as to whether there are changes in the interval between atrial sensed events or the interval between ventricular sensed events. In some examples this may be determined by looking at consecutive PP intervals and consecutive RR intervals. If there is a change in interval length outside of a range considered to be normal fluctuation, a determination may be made as to whether both the RR intervals and PP intervals are changing, and if they are changing in the same direction. That is, if a change in one interval is followed by a corresponding change in the other interval.

If the same interval (e.g., PP or RR) leads the change consistently, then that interval is determined to be the leading interval. Based on the leading interval, the associated chambers, either the atrium for a PP interval, or the ventricles for a RR interval, are determined to be leading the contractions of the heart. If the contractions are originating in the atrium, then the rhythm is classified as SVT. If the rhythm is originating in the ventricles, the rhythm is classified as VT or VF.

The classification scheme based on leading interval may be used in conjunction with a greater classification algorithm, such as one using both a NF EGM channel and a FF EGM channel during a classification. The leading interval classification scheme may also be used in conjunction with a classification algorithm that uses a sinus template.

In general, a post-processing classification may be used to evaluate prior classification of episodes by an IMD. An external device may reprogram and/or make modification to the operation of the implantable device based on the reclassification of one or more episodes by the external device.

FIG. 1 is a conceptual diagram illustrating an example system 10 for classifying a cardiac episode consistent with an example of the present disclosure. As illustrated in FIG. 1, a system for classifying episodes according to an example of the present disclosure includes an implantable medical device (IMD) 16, such as an implantable cardiac pacemaker, implantable cardioverter/defibrillator (ICD), or pacemaker/cardioverter/defibrillator, for example. IMD 16 is connected to leads 18, 20 and 22 and is communicatively coupled to a programmer 24.

IMD 16 senses electrical signal attendant to the depolarization and repolarization of heart 12, e.g., a cardiac electrogram (EGM), via electrodes on one or more leads 18, 20 and 22 or the housing of IMD 16. IMD 16 may also deliver therapy in the form of electrical signals to heart 12 via electrodes located on one or more leads 18, 20 and 22 or a housing of IMD 16, the therapy may be pacing, cardioversion and/or defibrillation pulses. IMD 16 may monitor EGM signals collected by electrodes on leads 18, 20 or 22, and based on the EGM signal diagnosis and treat cardiac episodes.

Programmer 24, or another external computing device, may evaluate the classifications made by IMD 16. A system for classifying episodes according to the present disclosure may additionally or alternatively include other medical devices, such as a cardiomyostimulator, a drug delivery system, cardiac and other physiological monitors, electrical stimulators including nerve, muscle and deep brain stimulators, cochlear implants and heart assist IMDs or pumps, for example.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. In some examples, the leads may be placed in different locations. For example, at least one lead may be on the outside of the heart. Although shown with leads 18, 20 and 22, in some examples IMD 16 may be include more or less leads.

In some examples, programmer 24 takes the form of a handheld computing device, mobile device, computer workstation or networked computing device that includes a user interface for presenting information to and receiving input from a user A user, such as a physician, technician, surgeon, electro-physiologist, or other clinician, may interact with programmer 24 to retrieve physiological or diagnostic information from IMD 16. A user may also interact with programmer 24 to program IMD 16, e.g., select values for operational parameters of the IMD. Programmer 24 may include a processor configured to evaluate EGM signals transmitted from IMD 16 to programmer 24. In some examples, as described in greater detail below, programmer 24 may evaluate a prior classification of an episode by IMD 16.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In some examples, programmer 24 may be located remotely from IMD 16, and communicate with IMD 16 via a network. Programmer 24 may also communicate with one or more other external devices using a number of known communication techniques, both wired and wireless.

In some examples, data acquired by IMD 16 can be monitored by an external system, such as the programmer 24. The classification of cardiac episodes according to an example of the present disclosure may take place in the programmer 24 once the required data is transmitted from IMD 16 to the programmer 24. IMD 16 may provide both a near-field and a far-field EGM signals to programmer 24. In some examples, programmer 24 or IMD 16 may transmit the required data to another external device, not shown in FIG. 1, for processing and classification.

Figure 2:
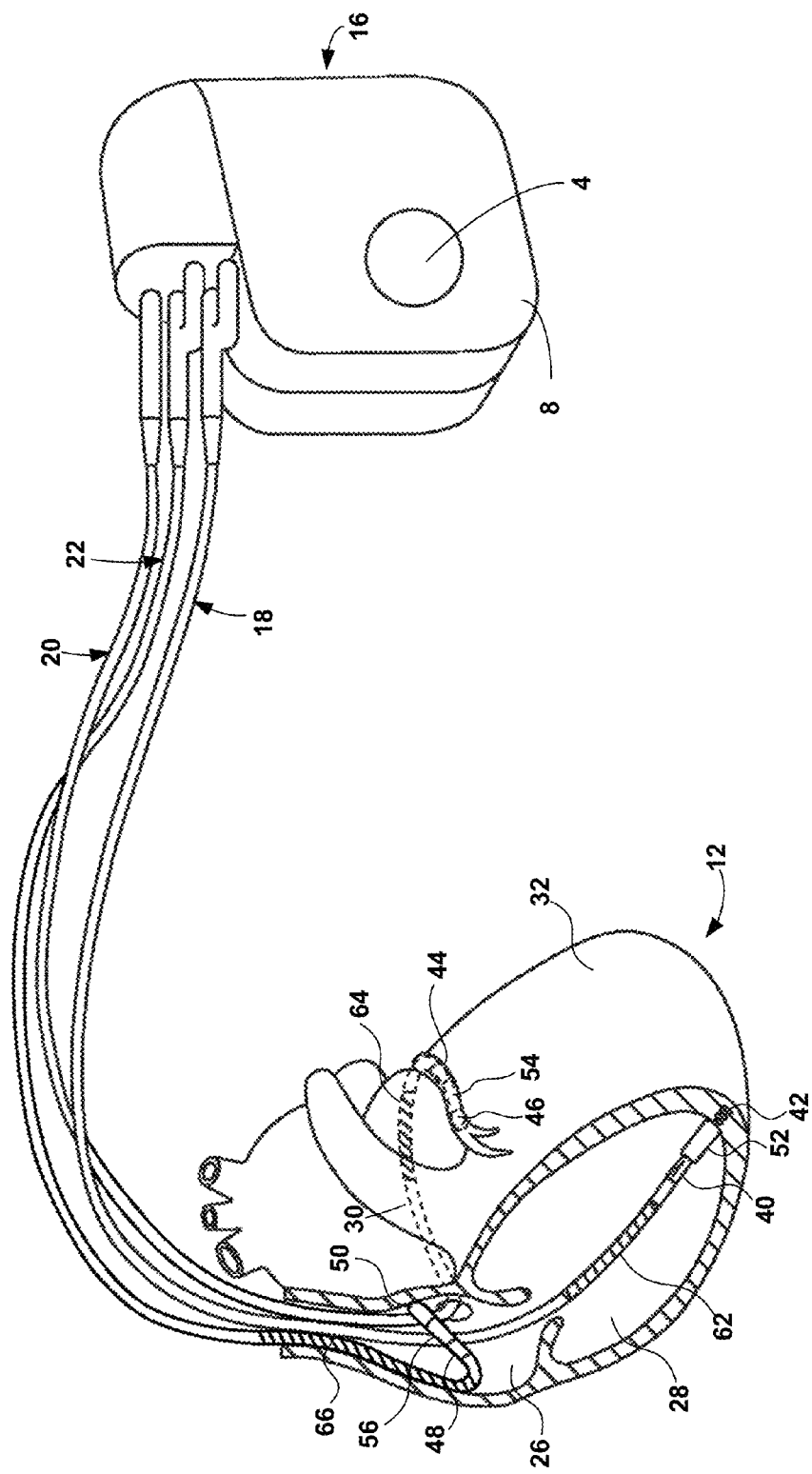
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative embodiments, not shown in FIG. 2, one or more of leads 18, 20 and 22, e.g., left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes 40, 42, 44, 46, 48, 50, 62, 64 and 66 is electrically coupled to a respective conductor within the lead body of its associated lead 18, 20, 22 and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

Housing 8 encloses a signal generator that generates therapeutic stimulation, such as cardiac pacing, cardioversion and defibrillation pulses, as well as a sensing module for sensing electrical signals attendant to the depolarization and repolarization of heart 12. Housing 8 may also enclose a memory for storing the sensed electrical signals. Housing 8 may also enclose a telemetry module for communication between IMD 16 and programmer 24.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

The illustrated numbers and configurations of leads 18, 20 and 22 and electrodes are merely examples. Other configurations, i.e., number and position of leads and electrodes, are possible. In some examples, system 10 may include an additional lead or lead segment having one or more electrodes positioned at different locations in the cardiovascular system for sensing and/or delivering therapy to patient 14. For example, instead of or in addition to intercardiac leads 18, 20 and 22, system 10 may include one or more epicardial or subcutaneous leads not positioned within the heart.

Figure 3:
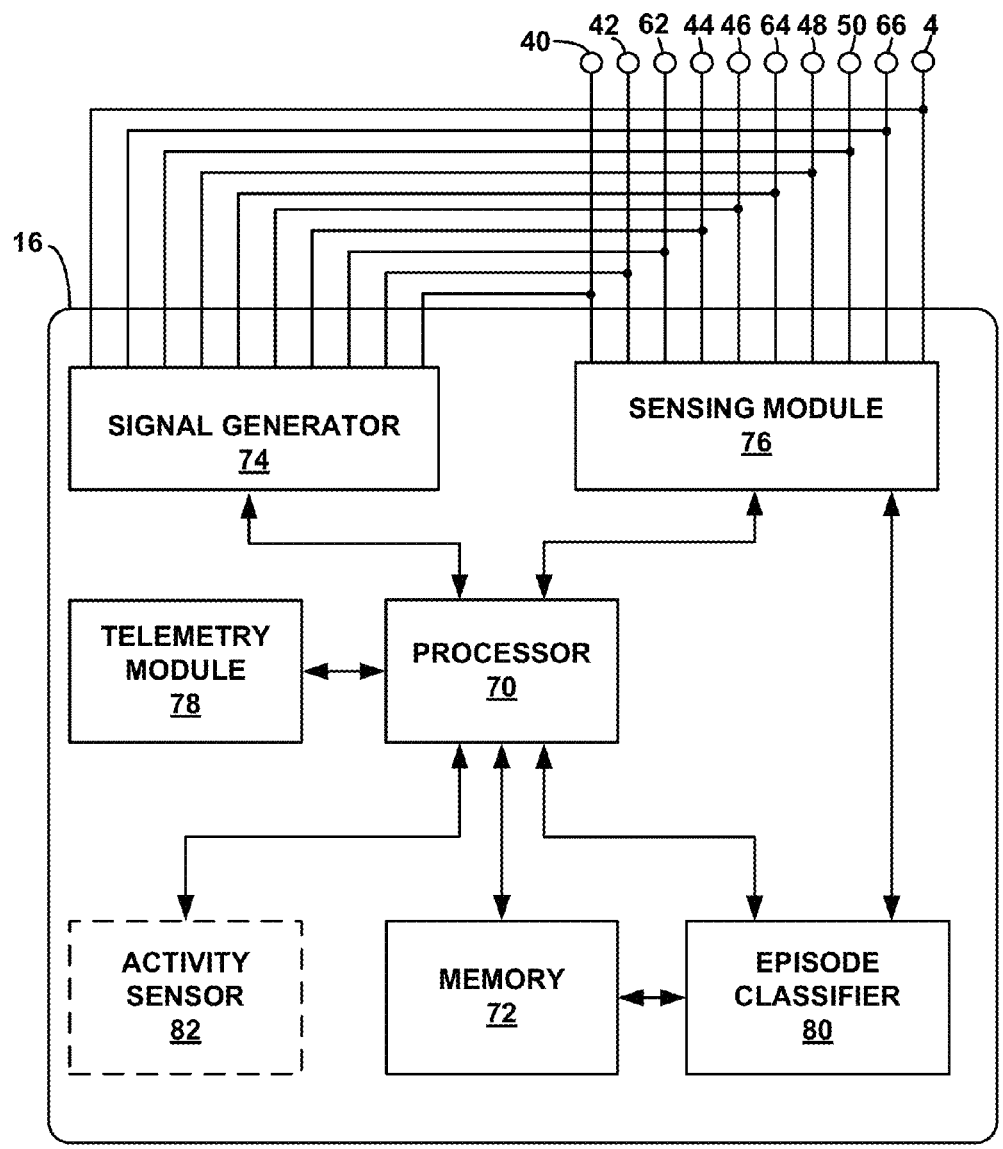
FIG. 3 is a block diagram illustrating an example IMD of FIG. 1.

FIG. 3 is a block diagram illustrating an example IMD 16 that monitors EGM signals and classifies the underlying cardiac rhythm as abnormal before providing a therapeutic response. In the illustrated example, IMD 16 includes a processor 70, memory 72, signal generator 74, sensing module 76, telemetry module 78, episode classifier 80, and activity sensor 82. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof.

Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs or parameters. In some examples, processor 70 may control signal generator 74 to deliver therapeutic stimulation responsive to a diagnosis or classification of an EGM signal by episode classifier 80.

Signal generator 74 is configured to generate and deliver electrical stimulation therapy to patient 14. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver pacing, defibrillation or cardioversion pulses to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70. One or more other detection channels may provide the signals to an analog-to-digital converter, for conversion into a digital signal for processing or analysis by processor 70 or episode classifier 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPA- RATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76 or processor 70. Processor 70 and/or episode classifier 80 may analyze the digitized version of signals from the wide band channel. Processor 70 and/or episode classifier 80 may employ digital signal analysis techniques to characterize the digitized signals from the wide band channel to, for example, detect and classify the patient's heart rhythm.

Episode classifier 80 may detect and classify the patient's heart rhythm based on the cardiac electrical signals sensed by sensing module 76 employing any of the numerous signal processing methodologies known in the art. For example, processor 70 may maintain escape interval counters that may be reset upon sensing of R-waves by sensing module 76. The value of the count present in the escape interval counters when reset by sensed depolarizations may be used by episode classifier 80 to measure the durations of RR intervals, which are measurements that may be stored in memory 72. Episode classifier 80 may use the count in the interval counters to detect a tachyarrhythmia, such as ventricular fibrillation or ventricular tachycardia. A portion of memory 72 may be configured as a plurality of recirculating buffers, capable of holding series of measured intervals, which may be analyzed by episode classifier 80 to determine whether the patient's heart 12 is presently exhibiting atrial or ventricular tachyarrhythmia.

In some examples, episode classifier 80 may determine that tachyarrhythmia has occurred by identification of shortened RR interval lengths. Generally, episode classifier 80 detects tachycardia when the interval length falls below 360 milliseconds (ms) and fibrillation when the interval length falls below 320 ms. These interval lengths are merely examples, and a user may define the interval lengths as desired, which may then be stored within memory 72. This interval length may need to be detected for a certain number of consecutive cycles, for a certain percentage of cycles within a running window, or a running average for a certain number of cardiac cycles, as examples.

In some examples, an arrhythmia detection method may include any suitable tachyarrhythmia detection algorithms. In one example, episode classifier 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. and U.S. Pat. No. 5,755,736 to Gillberg et al. are incorporated herein by reference in their entireties. However, other arrhythmia detection methodologies may also be employed by episode classifier 80 in some examples. For example, EGM morphology may be considered in addition to or instead of interval length for detecting tachyarrhythmias.

Generally, episode classifier 80 detects a treatable tachyarrhythmia, such as VF, based on the EGM, e.g., the RR intervals and/or morphology of the EGM, and, in response, processor 70 selects a therapy to deliver to terminate the tachyarrhythmia, such as a defibrillation pulse of a specified magnitude. The detection of the tachyarrhythmia may include a number of phases or steps prior to delivery of the therapy, such as first phase, sometimes referred to as detection, in which a number of consecutive or proximate RR intervals satisfies a first number of intervals to detect (NID) criterion, a second phase, sometimes referred to as confirmation, in which a number of consecutive or proximate RR intervals satisfies a second, more restrictive NID criterion. Tachyarrhythmia detection may also include confirmation based on EGM morphology or other sensors subsequent to or during the second phase. Again, in some cases, episode classifier 80 may mistakenly classify the patient's heart rhythm as a treatable tachyarrhythmia, e.g., as a result of a noisy EGM or misdiagnosis of a supraventricular tachyarrhythmia as being a ventricular tachyarrhythmia.

In some examples, episode classifier 80 has a portion of the EGM signal saved to memory 72 on an ongoing basis. When a tachyarrhythmia is not detected, the EGM signal may be written over after a period of time. In response to a tachyarrhythmia being detected, episode classifier 80 may direct memory 72 to store on a long-term basis a time period of the EGM signal leading up to the diagnosis of the tachyarrhythmia, along with the specific diagnosis, e.g., ventricular tachycardia, ventricular fibrillation, or supraventricular tachycardia.

Although processor 70 and episode classifier 80 are illustrated as separate modules in FIG. 3, processor 70 and episode classifier 80 may be incorporated in a single processing unit. Episode classifier 80 may be a component of or a module executed by processor 70.

Activity sensor 82 may be optionally included in some examples of IMD 16. Activity sensor 82 may include one or more accelerometers. Activity sensor 82 may additionally or alternatively include other sensor such as a heart sounds sensor, a pressure sensor, or an $O_2$ saturation sensor. Activity sensor 82 may detect respiration via one or more electrodes. Information obtained from activity sensor 82 may be used to determine activity level, posture, blood oxygen level or respiratory rate, for example, leading up to, or at the time of the abnormal heart rhythm. In some examples, this information may be used by IMD 16 to aid in the classification of an abnormal heart rhythm.

Activity sensor 82 may, for example, take the form of one or more accelerometers, or any other sensor known in the art for detecting activity, e.g., body movements or footfalls, or posture. In some examples, activity sensor 82 may comprise a three-axis accelerometer. Processor 70 may determine an activity level count at regular intervals based on the signal(s) from activity sensor 82. In some examples, processor 70 may determine a running average activity count based on the information provided by activity sensor 82. For example, the activity count may be calculated over a 1 second interval and the processor 70 may update the activity level count at a 1 second interval. A method of determining activity count from an accelerometer sensor is described in U.S. Pat. No. 6,449,508, to Sheldon et al, entitled, "ACCELEROMETER COUNT CALCULATION FOR ACTIVITY SIGNAL FOR AN IMPLANTABLE MEDICAL DEVICE," issued Sep. 10, 2002, and incorporated herein by reference in its entirety.

Activity sensor 82 may be located outside of the housing 8 of IMD 16. Activity sensor 82 may be located on a lead that is coupled to IMD 16 or may be implemented in a remote sensor that wirelessly communicates with IMD 16 via telemetry module 78. In any case, activity sensor 82 is electrically or wirelessly coupled to circuitry contained within housing 8 of IMD 16.

Telemetry module 78 includes any suitable hardware, firmware, software or any combination thereof for communicating with another device, such as programmer 24 (FIG. 1). Under the control of processor 70, telemetry module 78 may receive downlink telemetry from and send uplink telemetry to programmer 24 with the aid of an antenna, which may be internal and/or external. In some examples, processor 70 may transmit cardiac signals, e.g., ECG or EGM signals, produced by sensing module 76 and/or signals selected by episode classifier 80 to programmer 24. Processor 70 may also generate and store marker codes indicative of different cardiac or other physiological events detected by sensing module 76 or episode classifier 80, and transmit the marker codes to programmer 24. An example IMD with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety. Information which processor 70 may transmit to programmer 24 via telemetry module 78 may also include an indication of a change in disease state of the heart, an indication of a change in heart response to the therapy provided or an indication that the heart continues to response in the same (or similar) manner to the therapy provided, the indications based on heart sounds and/or EGM signals. Such information may be included as part of a marker channel with an EGM.

Figure 4:
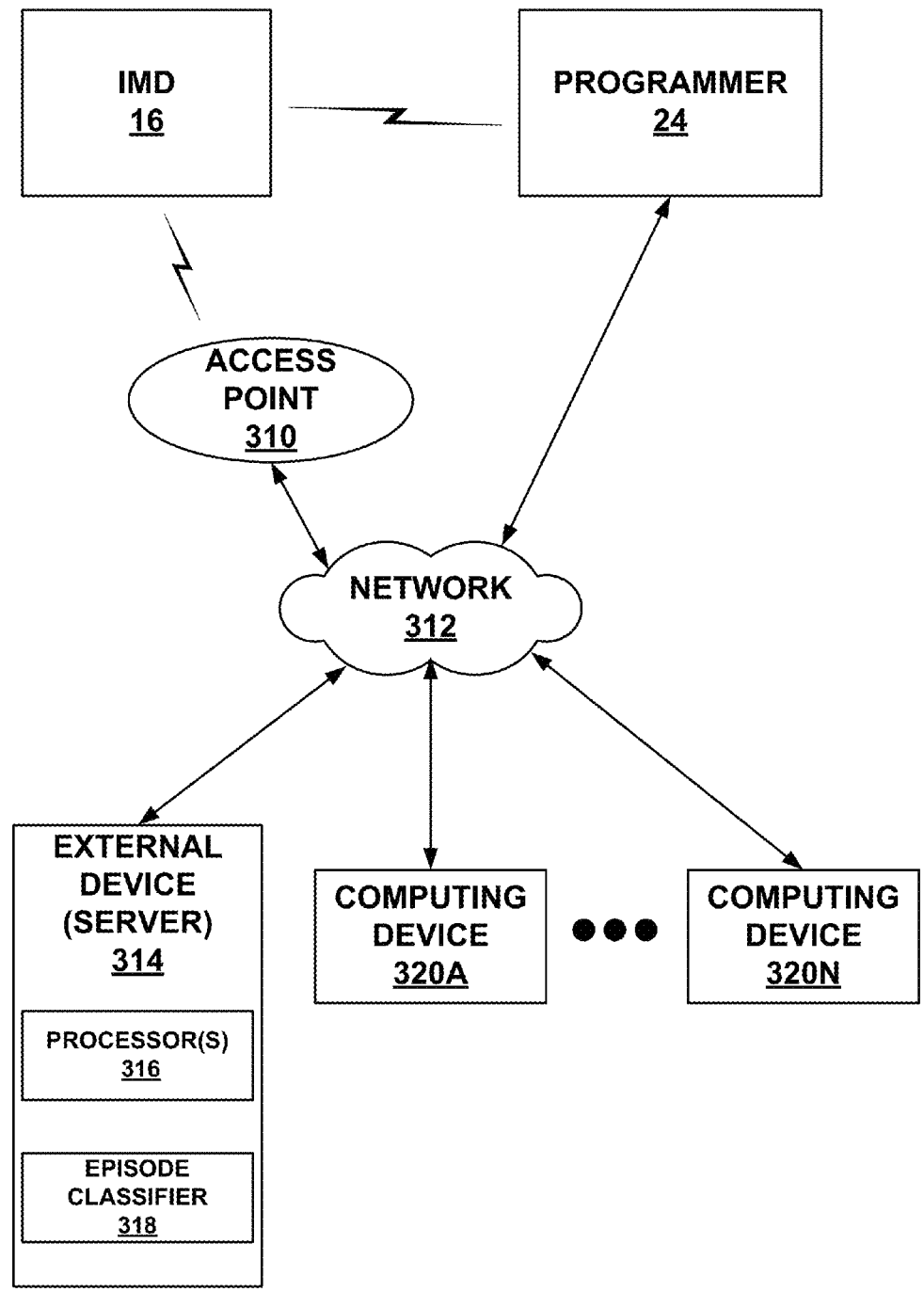
FIG. 4 is a block diagram illustrating an example system that includes and external device, such as a server, and one or more computing devices that are coupled to the IMD and programmer shown in FIG. 1 via a network.

FIG. 4 is a block diagram illustrating an example system that includes an external device, such as a server 314, and one or more computing devices 320A-320N that are coupled to the IMD 16 and programmer 24 shown in FIG. 1 via a network 312. Network 312 may be generally used to transmit diagnostic information (e.g., a diagnosis made by IMD 16 resulting in a shock) from an IMD 16 to a remote external computing device. In some examples, EGM signals may be transmitted to an external device for processing.

In some examples, the information transmitted by IMD 16 may allow a clinician or other healthcare professional to monitor patient 14 remotely. In some examples, IMD 16 may use a telemetry module to communicate with programmer 24 via a first wireless connection, and to communicate with access point 310 via a second wireless connection, e.g., at different times. In the example of FIG. 4, access point 310, programmer 24, server 314 and computing devices 320A-320N are interconnected, and able to communicate with each other through network 312. In some cases, one or more of access point 310, programmer 24, server 314 and computing devices 320A-320N may be coupled to network 312 via one or more wireless connections. IMD 16, programmer 24, server 314, and computing devices 320A-320N may each comprise one or more processors, such as one or more microprocessors, DSPs, ASICs, FPGAs, programmable logic circuitry, or the like, that may perform various functions and operations, such as those described herein.

Access point 310 may comprise a device that connects to network 312 via any of a variety of connections, such as telephone dial-up, digital subscriber line (DSL), or cable modem connections. In other examples, access point 310 may be coupled to network 312 through different forms of connections, including wired or wireless connections. In some examples, access point 310 may be co-located with patient 14 and may comprise one or more programming units and/or computing devices (e.g., one or more monitoring units) that may perform various functions and operations described herein. For example, access point 310 may include a home-monitoring unit that is co-located with patient 14 and that may monitor the activity of IMD 16. In some examples, server 314 or computing devices 320 may control or perform any of the various functions or operations described herein, e.g., determine, based on EGM signal data, an episode classification using episode classifier 318 to determine if IMD 16 properly classified various cardiac episodes.

In some cases, server 314 may be configured to provide a secure storage site for archival of diagnostic information (e.g., occurrence of a diagnosis and shock by IMD 16 and attendant circumstances such as the EGM signal leading up to the diagnosis) that has been collected and generated from IMD 16 and/or programmer 24. Network 312 may comprise a local area network, wide area network, or global network, such as the Internet. In some cases, programmer 24 or server 314 may assemble EGM signal and diagnosis information in web pages or other documents for viewing by trained professionals, such as clinicians, via viewing terminals associated with computing devices 320. The system of FIG. 4 may be implemented, in some aspects, with general network technology and functionality similar to that provide by the Medtronic CareLink® Network developed by Medtronic, Inc., of Minneapolis, Minn.

In the example of FIG. 4, external server 314 may receive EGM signal data from IMD 16 via network 312. Based on the EGM signal data received, processor(s) 316 may preform one or more of the functions described herein with respect to processor 86 of programmer 24. Computing devices 320A-320N may also include a processor that performs one or more of the functions described herein with respect to processor 86 of programmer 24. For example, episode classification may be carried out by any of the programmer 24, external server 314 or computing device 320.

Figure 5:
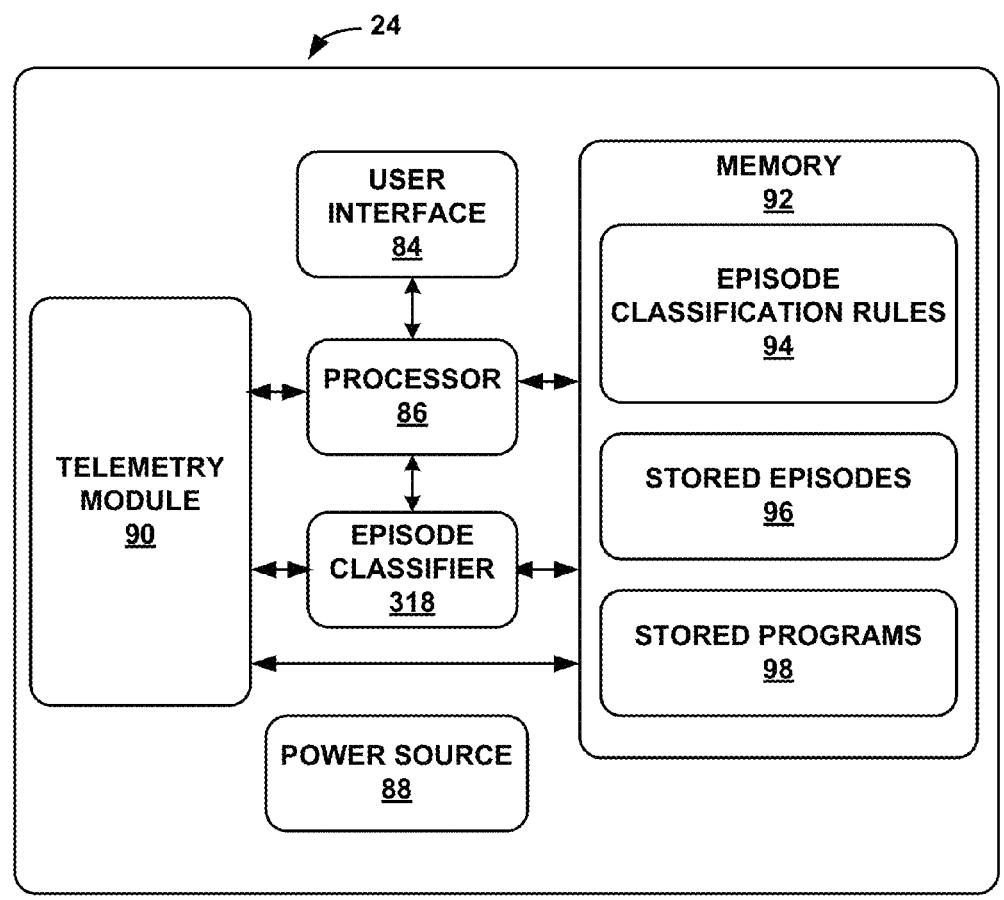
FIG. 5 is a block diagram illustrating an example programmer of FIG. 1.

FIG. 5 is a block diagram illustrating an example programmer 24 of FIG. 1. As illustrated in FIG. 5 programmer 24 may include a processor 86, a memory 92, a user interface 84, a telemetry module 90, an episode classifier 318, and a power source 88. Processor 86 stores and retrieves information and instructions to and from memory 92. Programmer 24 may be configured for use as a clinician programmer of a patient programmer. Processor 86 may include a microprocessor, a microcontroller, a DSP, an ASIC, an FPGA, or other equivalent discrete or integrated logic circuitry. Accordingly, processor 86 may include any suitable structure, whether in hardware, software, firmware or any combination thereof, to perform the functions ascribed herein to processor 86.

A user, such as a clinician, may interact with programmer 24 through user interface 84. Accordingly, in some examples programmer 24 may comprise a patient programmer or a clinician programmer. The techniques of this disclosure are directed post-processing of EGM signals collected by IMD 16 and used by IMD 16 to diagnosis treatable arrhythmias. The post-processing is used to determine whether IMD 16 correctly diagnosed the detected arrhythmia. Therefore, many of the functions ascribed to programmer 24, and in particular processor 86, may be performed by any external device, e.g., external device 314, or computing device, e.g., computing device 320. When programmer 24 is configured as a patient programmer, in some examples, the patient programmer is not necessarily configured to perform the post-processing or provide information regarding the accuracy of diagnosis to the patient. In some examples, when programmer 24 is configured as a clinician programmer, processor 86 may be configured to perform the post-processing using episode classifier 318 and episode classification rules 94.

Although processor 86 and episode classifier 318 are illustrated as separate modules in FIG. 5, processor 86 and episode classifier may be incorporated in a single processing unit. Episode classifier 318 may be a component of or a module executed by processor 86.

User interface 84 includes a display (not shown), such as a LCD or LED display or other type of screen, to present information related to the therapy, such as information related to current stimulation parameters and electrode combinations and in some examples, when configured to render graphics objects, an image of a volume of activation and an anatomical feature including a therapy target of patient 14. In addition, user interface 84 may include an input mechanism to receive input from the user. The input mechanisms may include, for example, buttons, a keypad (e.g., an alphanumeric keypad), a peripheral pointing device, or another input mechanism that allows the user to navigate through user interfaces presented by processor 86 of programmer 24 and provide input. The input may include, for example, changes to current or proposed stimulation parameters or selection of electrode combinations.

If programmer 24 includes buttons and a keypad, the buttons may be dedicated to performing a certain function, e.g., a power button, or the buttons and the keypad may be soft keys that change in function depending upon the section of the user interface currently viewed by the user. Alternatively, the display (not shown) of programmer 24 may be a touch screen that allows the user to provide input directly to the user interface shown on the display. The user may use a stylus or a finger to provide input to the display. In other examples, user interface 84 also includes audio circuitry for providing audible instructions or sounds to patient 14 and/or receiving voice commands from patient 14, which may be useful if patient 14 has limited motor functions. Patient 14, a clinician or another user may also interact with programmer 24 to manually select therapy programs, generate new therapy programs, modify therapy programs through individual or global adjustments, and transmit the new programs to IMD 16. In some examples, at least some of the control of therapy delivery by IMD 16 may be implemented by processor 86 of programmer 24. A clinician or other user may interact with programmer 24 to select a stimulation electrode combination or modify a set of stimulation parameters.

In some examples, processor 86 may control IMD 16 via telemetry module 90 to modify program parameters controlling a stimulator within IMD 16 to deliver cardiac stimulating pulses to heart 12 via selected electrode combinations. In particular, processor 86 transmits programming signals to IMD 16 via telemetry module 90. Processor 86 receives a segment of EGM signal data containing representing a cardiac episode resulting in a diagnosis of an arrhythmia followed by electrical stimulation based on the diagnosis. The episode may be received from telemetry module 90 or from memory 92.

Episode classifier 318 may apply episode classification rules stored in episode classification rules 94 to the cardiac episode. The episodes received from IMD 16 may be stored in stored episodes 96 until retrieved by episode classifier 318 for classification.

Telemetry module 90 receives EGM signal data from IMD 16. The EGM signal data may be transmitted to telemetry module 90 when IMD 16 diagnoses an arrhythmia and responds with electrical stimulation. In some examples, portions of EGM signal data are stored in memory 72 of IMD 16 until a predetermined event occurs. After the event has occurred the data is transmitted via telemetry module 78 of IMD 16 to telemetry module 90 of programmer 24. For example, periodically, e.g., every three months, or opportunistically, e.g., when IMD 16 is in communication with programmer 24 or access point 310, IMD 16 may transmit EGM signal data selected by episode classifier 80 and stored in memory 72. In some examples telemetry module 90 sends program information to IMD 16 to control the operation of the IMD.

In some examples, shown in FIG. 5, memory 92 includes episode classification rules 94, stored episodes 96 and stored programs 98 in separate memories within memory 92 or separate areas within memory 92. Memory 92 may also include instructions for operating user interface 84, telemetry module 90, and for managing power source 88. Memory 92 may include any volatile or nonvolatile memory such as RAM, ROM, EEPROM or flash memory. Memory 92 may also include a removable memory portion that may be used to provide memory updates or increases in memory capacities. A removable memory may also allow sensitive patient data to be removed before programmer 24 is used by a different patient.

Stored episodes 96 stores EGM signal data received from IMD 16 via telemetry module 90. In some examples, the EGM signal data is separated into episodes, and each episode is saved along with a diagnosis made by IMD 16 based on the EGM signal data in the episode. IMD 16 may transmit EGM signal data at predetermined time intervals, for example every three months. The EGM signals are received by telemetry module 90 and stored in stored episodes 96 until a classification algorithm is initiated. In some examples, episode classifier 318, retrieves episodes stored in stored episodes 96 one at a time and confirms or rejects the diagnosis of IMD 16 using episode classification rules stored in episode classification rule 94. In some examples, a user may select one or more episodes stored in stored episodes 96 for post-processing classification.

Episode classification rules 94 store a classification algorithm or a set of classification rules used to confirm or reject the diagnosis of IMD 16. In some examples, the classification algorithm is as shown in FIGS. 6A-6C or FIG. 7, and described in more detail below. In some examples, the episode classification rules classify each episode as supraventricular tachycardia (SVT), ventricular tachycardia or ventricular fibrillation (VT/VF) or unknown. The classifications may be compared to the diagnosis generated by IMD 16 prior to delivery therapy, for example.

Figure 6A:
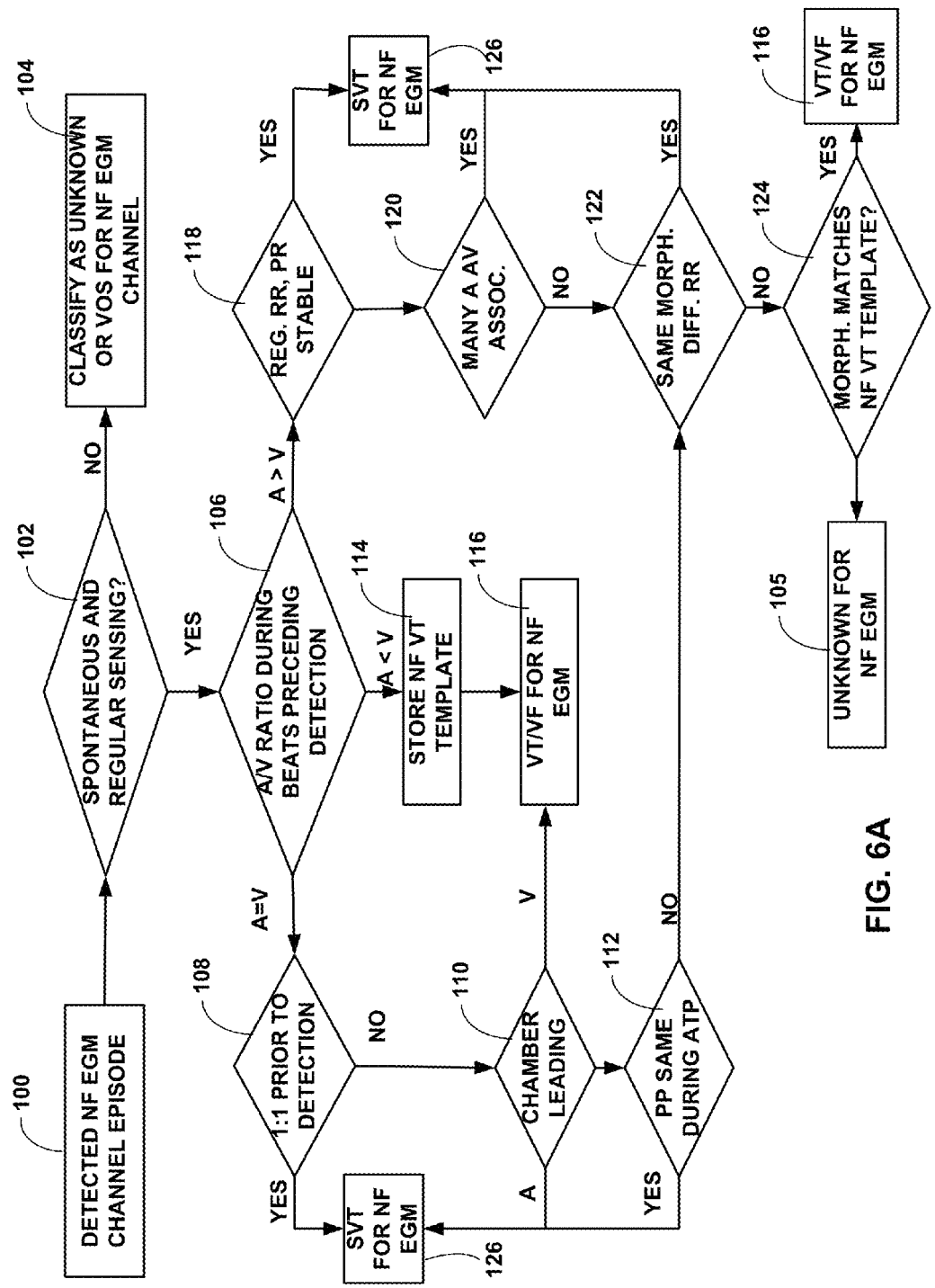
FIG. 6A is a flow chart illustrating an example episode classification algorithm for an EGM signal on a near-field channel.
Figure 6B:
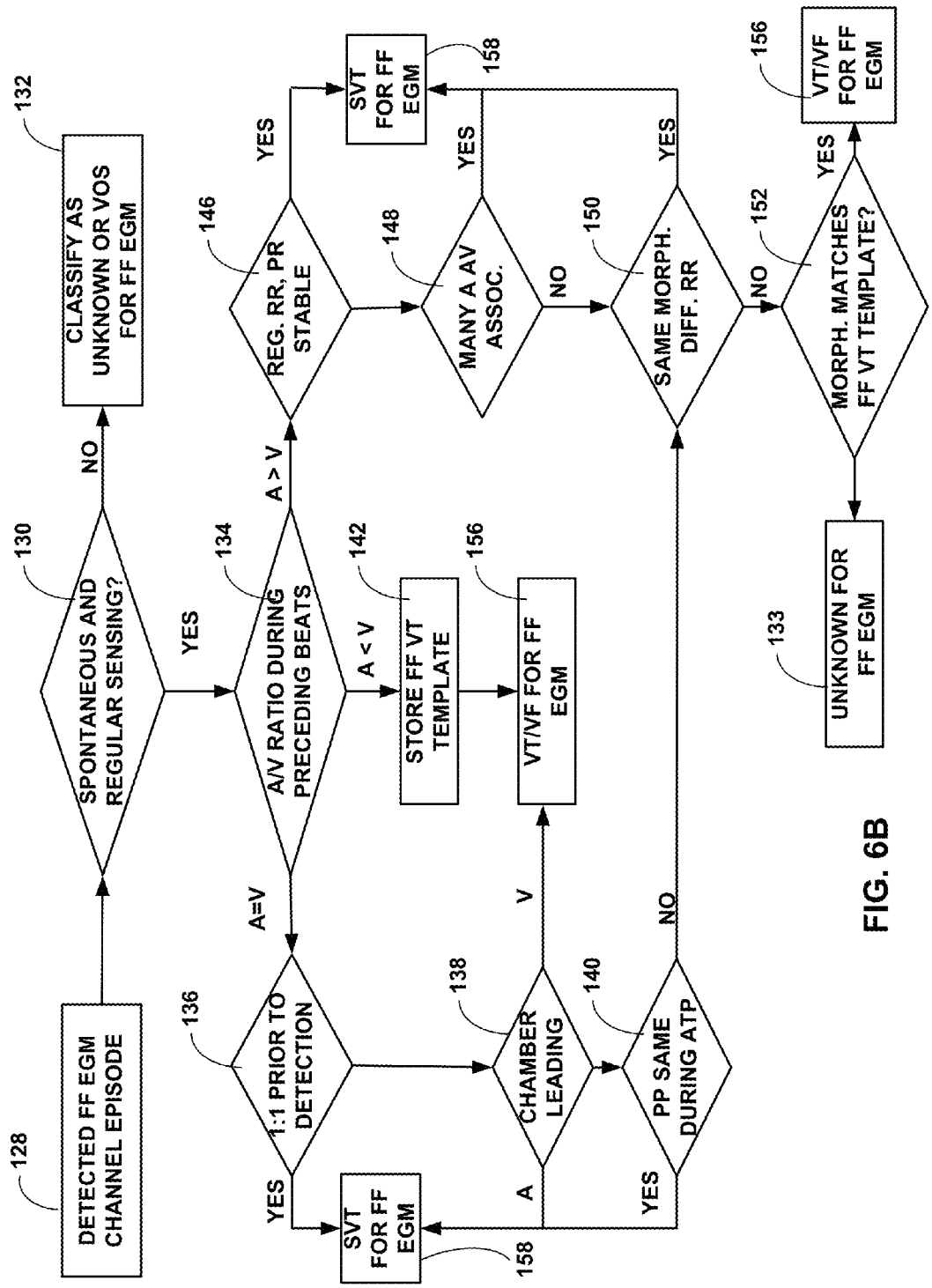
FIG. 6B is a flow chart illustrating an example episode classification algorithm for an EGM signal on a far-field channel.
Figure 6C:
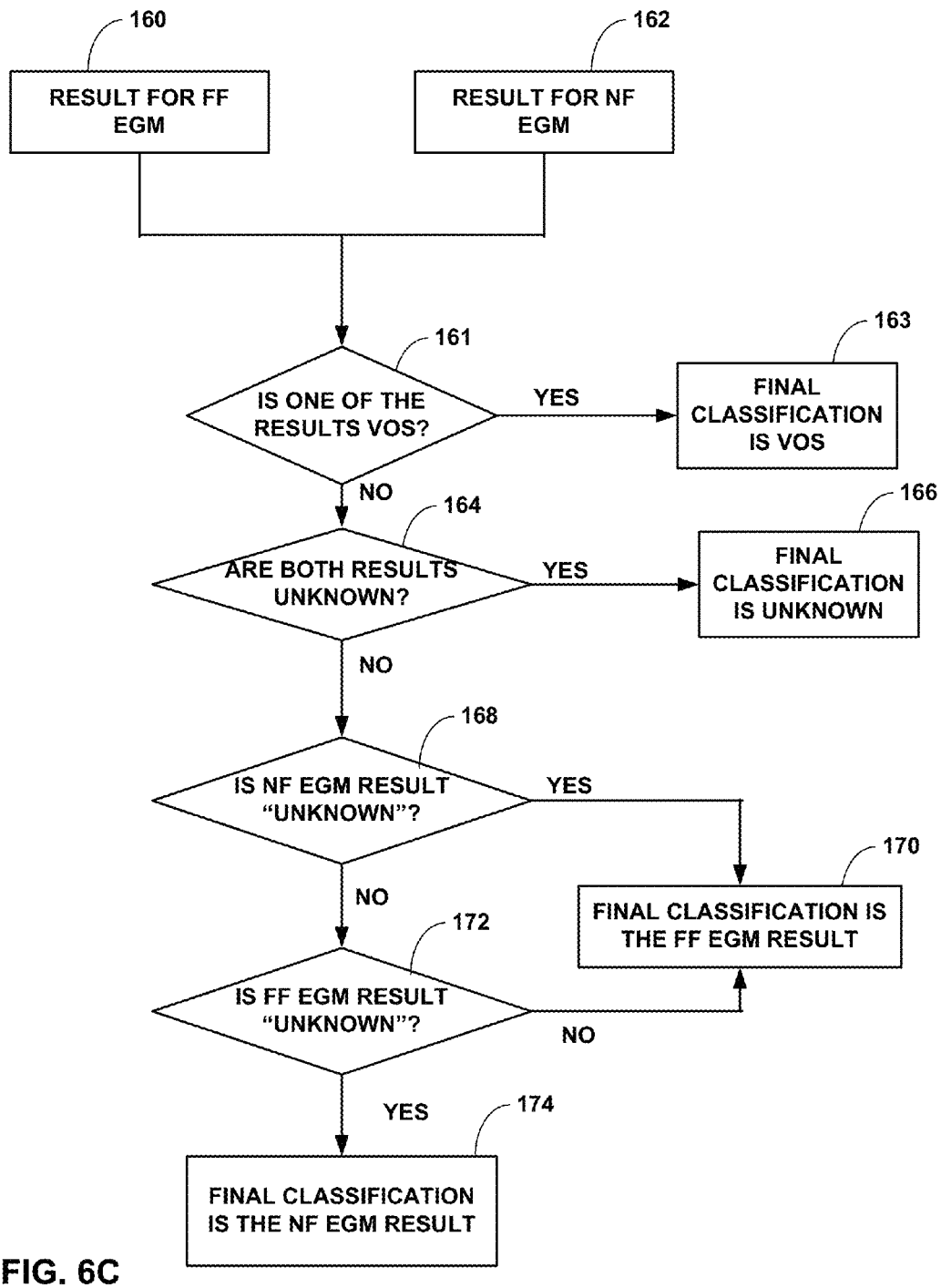
FIG. 6C is a flow chart illustrating an example method of determining a final classification for an episode classified on both a near-field channel and a far-field channel.

FIGS. 6A-6C are parts of a flow chart illustrating an example classification algorithm consistent with the present disclosure. The example classification algorithm of FIGS. 6A-6C is generally applicable to cardiac episodes where IMD 16 stored EGM signals for both the NF and FF channels. FIG. 6A illustrates a classification algorithm using EGM signal data from a near-field (NF) EGM channel. FIG. 6B illustrates a classification algorithm using EGM signal data from a far-field (FF) EGM channel. FIG. 6C illustrates a classification algorithm for determining a final classification based on the classification of the NF EGM data and the FF EGM data. The NF and FF portions of the algorithm illustrated in FIGS. 6A and 6B may be applied in any order. The resulting classification is stored, and the classification from both FIG. 6A and FIG. 6B are used in FIG. 6C.

Turning to FIG. 6A, episode classifier 318 selects a detected NF EGM Channel episode (100) from stored episodes 94. Episode classifier 318 determines whether the EGM data received from IMD 16 includes spontaneous and regular sensing (102), i.e., not induced. In some examples, a method of determining whether data previously utilized by a device to identify a cardiac episode correspond to regular sensing of events includes a determination as to whether over-sensing or under-sensing has occurred. The determination of over-sensing or under-sensing may be based on a determination of whether one of a predetermined number of over-sensing or under-sensing criteria has been met. An example of an over-sensing criterion includes the existence of simultaneous atrial and ventricular events, except in instances where the ventricular event is ventricular Pace for ATP. An example of an under-sensing criterion includes determining whether at least one sensed AA interval associated with predetermined beats, such as the NID ventricular beats prior to detection of the event and the atrial interval immediately subsequent to the detection of the event is greater than a predetermined interval, such as 2500 ms, for example. Another example of under-sensing criteria include determining whether the atrial channel includes less than a predetermined number of events prior to detection. Other examples of both over-sensing and under-sensing criteria are taught in U.S. Pat. No. 7,894,883 to Gunderson et al., incorporated herein by reference in its entirety. In the event that an episode is found to be either not spontaneous or not include regular sensing, the episode is classified as unknown or ventricular over-sensing (VOS) for the NF EGM channel (104). The episode may be categorized as VOS when over-sensing is found.

In response to a determination that the episode received from IMD 16 is spontaneous and includes regular sensing, episode classifier 318 and/or processor 86 determine the A/V (atrial events to ventricular events) ratio during the beats preceding detection (106) or diagnosis. The ratio of atrial sensed events to ventricular sensed events is determined for a predetermined window of sensed events occurring prior to detection or diagnosis by IMD 16 of the cardiac episode. In some examples, the predetermined window used for calculating the A/V ratio may be defined by the last 12 ventricular sensed events occurring just prior to the point of diagnosis of the cardiac episode. It is understood that the window may be defined by any predetermined number of ventricular sensed events prior to detection. The number of atrial sensed events occurring within the window is then determined and used to determine the A/V ratio. If the number of atrial sensed events occurring during the window is equal to the number of ventricular sensed events, a determination is made as to whether the atrial sensed events are evenly distributed with the ventricular sensed events, that is, whether there is a 1:1 distribution prior to detection (108). If there is one atrial sensed event located between each adjacent pairs of all of the ventricular sensed events, the event is identified as being a supraventricular tachycardia (SVT) episode (126) for the NF EGM Channel. The rationale behind this classification is that a ventricular arrhythmia would have a shorter ventricular cycle length than the atrial cycle length at some point in the episode.

If the atrial sensed events are determined to be not evenly distributed with the ventricular sensed events in a one to one distribution (108) the classification of the episode is further evaluated. Episode classifier 318 may determine which chamber is leading (110). Episode classifier 318 determines whether the heart rhythm was initiated by conduction in the ventricles or in the atria. In some examples, an onset threshold is determined. Once the onset threshold has been determined, a spatial reference point is identified and used to form a window for determining whether conduction of the heart rhythm was imitated by one of the atrial and the ventricular chambers. For example, an RR interval associated with pre-NID or sinus rhythm, i.e., greater than the onset threshold, occurring prior to an interval correspond to when the episode was detected, may be used as the spatial reference point for forming the window. In some examples, the spatial reference point may be identified by determining by working backwards from the detection until a predetermined number of sequential adjacent intervals occurring prior to the interval associated with the detection is greater than the onset threshold. Other examples of determining a spatial reference point and window for determining which chamber is leading may be found in U.S. Pat. No. 7,894,883 to Gunderson et al., incorporated herein by reference in its entirety.

Determining which chamber is leading (110) may include identification of a spatial reference point, as wells as a predetermined number of intervals centered around the determined spatial reference point. The number of sensed atrial events occurring between each interval within the window is determined. If there is one atrial sensed event between each of the adjacent ventricular sensed events in the window, the atrium is determined to be initiating conduction. In response to a determination that the atrium is leading, episode classifier 318 classifies the episode as SVT for the NF EGM channel (126). If there is one atrial sensed event between adjacent ventricular sensed events for all except one of the ventricular sensed event intervals, and no atrial sensed events between one set of adjacent ventricular sensed events, then the ventricles are determined to be initiating conduction. If the ventricles are found to be leading, episode classifier 318 classifies the episode as a ventricular tachycardia/ventricular fibrillation (VT/VF) episode (116). If there is one atrial sensed event between each of the adjacent ventricular sensed events for less than the number of intervals minus one, and no atrial sensed event between adjacent ventricular sensed events for more than one of the intervals, then neither the atrium nor the ventricles are determined to be driving conduction. If no determination is made, then processor 86 continues to attempt to classify the episode based on whether the effects the effects of anti-tachycardia pacing (ATP) are indicative of a supraventricular tachycardia episode.

Episode classifier 318 may determine whether the cycle length between atrial events, that is, the interval between P-waves is the same during the episode being classified as during an antitachycardia pacing regimen previously applied to the patient (112). In some examples, a determination about the effects of anti-tachycardia pacing is made using a method of dynamic discrimination described in commonly assigned U.S. Pat. No. 7,317,942, issued Jan. 8, 2008, entitled "DYNAMIC DISCRIMINATION UTILIZING ANTI-TACHY PACING THERAPY IN AN IMPLANTABLE MEDICAL DEVICE" to Brown et al., and incorporated herein by reference in its entirety. For example, instances where IMD 16 delivered an antitachycardia pacing regimen may be identified by IMD 16 or programmer 24 and the corresponding EGM signal data may be stored in memory 92. The EGM signal associated with the therapy may be reviewed to determine a mean cycle length between atrial events occurring prior to the delivery of the antitachycardia pacing therapy and comparing the determined atrial cycle length during the delivery of the pacing therapy to a mean cycle atrial cycle length during the episode. If the difference between the mean atrial cycle and the atrial cycle length during the delivery of the pacing therapy is less than or equal to a predetermined atrial cycle length threshold, such as 30 ms for example, the episode is classified as being a SVT on the NF channel (126). If the difference between the mean atrial cycle length for the episode and the atrial cycle length during the delivery of the pacing therapy is greater than the predetermined threshold then the processor continues with the classification algorithm for the NF EGM channel.

If the PP interval (or atrial cycle) of the episode is not the same as the atrial cycle length during ATP, then the morphology of a maximum interval within the episode being classified and the minimum interval within the episode being classified are compared. Episode classifier 318 may determine, based on episode classification rules 94, whether the intervals have the same morphology despite having different RR interval lengths (122). In some examples, the comparison occurs if the difference between the maximum interval and the minimum interval is greater than a predetermined threshold. A determination is then made as to whether the correlation between the morphologies of the two intervals is greater than a predetermined correlation threshold, such as 0.94, for example.

If the correlation between the two intervals is greater than the predetermined correlation threshold, then the detected episode is classified as being SVT for the NF EGM channel (126). If the correlation is below the predetermined correlation threshold, or the difference between the maximum and minimum intervals is below the predetermined threshold for difference between the two intervals, then the morphology of the intervals within the episode are compared to a NF VT template. Episode classifier 318 determines how many of the intervals have a morphology that matches the NF VT template (124). The NF VT template may be one of more NF VT templates stored within memory 92. In some examples the VT template may have been stored during the classification of a previous episode from the same patient. Episode classifier 318 compares each interval within the episode with the NF VT template and determines whether each interval correlates to the NF VT template based on a predetermined correlation threshold. If the number of intervals having morphologies that correlate to the NF VT template is above a predetermined matching percentage threshold, then the morphology for the episode is determined to match the template. In response, the episode is classified at VT/VF for the NF EGM channel (116). If the number of intervals having morphologies that correlate to the NF VT template is below the predetermined matching percentage threshold, then the episode is classified as unknown for the NF EGM channel (105). The matching percentage threshold may be programmable by a default, or may be adjusted by the clinician or other user. In some examples the threshold may be adjusted on a patient-by-patient or clinic-by clinic basis. In some examples, the matching percentage threshold may be between approximately 70% and 85%. In some examples, the matching percentage threshold may be approximately 80%.

If that the A/V ratio during the beats preceding detection (106) is such that the number of atrial sensed events is below the number of ventricular sensed events within a window preceding detection, then an interval may be stored as a NF VT template (114). The episode is classified as VT/VF for the NF EGM channel (116). In some examples, the difference between the number of atrial sensed events and the number of ventricular sensed events must be greater than 1.

In response to an A/V ratio during the beats preceding a detection (106) where the number of atrial sensed events is greater than the number of ventricular sensed events, episode classifier 318 determines whether the data used by IMD 16 during the initial classification of the episode as a detected episode includes RR intervals that are regular, and whether the PR intervals are stable (118). In an example to illustrate how episode classifier 318 determines whether the RR intervals are regular and whether the PR intervals are stable (118), an episode being processed includes a number of intervals to detection (NID) of 16 intervals. That is, during the initial detection process IMD 16 detected the occurrence of a cardiac episode once the detection criteria had been met, i.e., once 16 intervals having a rate than the threshold rate were detected. In some examples, IMD 16 continuously stores a buffer containing a number of the most recent intervals of the EGM signal. This may allow IMD 16 to store an EGM signal including all 16 intervals resulting in detection to memory 72 after detection. In order to determine whether the data used by IMD 16 during the initial classification of the episode as a detected episode includes intervals that are regular, a modesom of the 16 RR intervals resulting in detection is generated by determining whether the number of intervals in the two highest modes (i.e., most frequent bins) is greater than a predetermined percentage of the number of RR intervals. The percentage may be 67%, for example. If the number of intervals in the two highest modes is above the percentage threshold, then the data is considered to include regular RR intervals.

Episode classifier 318 also determines whether the AV intervals associated with the initial identification of the episode as a cardiac episode are stable. For example, in order to determine whether the AV intervals associate with the initial identification of the episode as a cardiac episode are stable, PR intervals, i.e., the time between an atrial sensed event and a subsequent ventricular sensed event, are determined for each of the 16 intervals. In some examples, in order to reduce the effect of outliers, once the PR intervals are determined for each of the intervals associated with the initial identification of the episode as a cardiac episode, a predetermined number of maximum PR intervals and minimum PR intervals are removed. For example, one sixth of the maximum PR intervals and one sixth of the minimum PR intervals may be removed. A PR range is then determined as the difference between the minimum PR interval and the maximum PR interval. Episode classifier 318 then determines whether the range of PR intervals satisfies a PR stable criterion. For example, a determination may be made as to whether the range of the remaining PR intervals is less than 20 ms. In response to a determination that the RR intervals are regular and the PR intervals are stable, the episode is classified as SVT for the NF EGM channel (126). If episode does not include both regular RR intervals and stable PR intervals, then episode classifier 318 determiners how many atrial events are unassociated with a ventricular event and how many atrial events are associated with a ventricular event (120). The episode classifier 318 may look for approximately consistent AV intervals for atrial events associated with a ventricular event. If the number of atrial events part of an AV interval is above a predetermine threshold, then the cardiac episode is classified as SVT for the NF EGM channel (126) by episode classifier 318.

If the number of unassociated atrial events is below a predetermined threshold, then, the data associated with the episode is examined to determine whether RR intervals with different lengths have approximately the same morphology (122). In some examples, the maximum and minimum intervals in the episode are compared and, if the difference is greater than a predetermined threshold, such as 100 ms for example, then the morphology of the maximum interval is compared to the morphology of the minimum interval. If the morphologies are found to correlate, the episode is classified as SVT for the NF EGM channel (126). As described above, if the maximum and minimum intervals are not found to correlate, then the morphologies of each of the intervals associated with detection of a cardiac episode are compared with a template or templates stored in memory 82, the template or templates being NF VT templates. Episode classifier 318 determines for each of the intervals whether the correlation of the morphology between the interval and the template is greater than a predetermined correlation threshold. If then number of intervals having morphologies that correlate to the store template is greater than a predetermined matching percentage threshold, than the episodes is classified as being VT/VF for the NF channel. If the number of intervals that match is below the matching percentage threshold, then the episode is classified as unknown for the NF EGM channel (105).

FIG. 6B illustrates an example algorithm for classifying EGM data received from the FF channel of IMD 16. Episode classifier 318 selects a detected NF EGM Channel episode (128) from stored episodes 94. Processor 86 and/or episode classifier 318 determines whether the EGM data received from IMD 16 includes spontaneous and regular sensing (130), i.e., not induced. In some examples, a method of determining whether data previously utilized by a device to identify a cardiac episode correspond to regular sensing of events includes a determination as to whether over-sensing or under-sensing has occurred. The determination of over-sensing or under-sensing may be based on a determination of whether one of a predetermined number of over-sensing or under-sensing criteria has been met. An example of an over-sensing criterion includes the existence of simultaneous atrial and ventricular events, except in instances where the ventricular event is ventricular Pace for ATP. An example of an under-sensing criterion includes determining whether at least one sensed AA interval associated with predetermined beats, such as the NID ventricular beats prior to detection of the episode and the atrial interval immediately subsequent to the detection of the episode is greater than a predetermined interval, such as 2500 ms, for example. Another example of under-sensing criteria include determining whether the atrial channel includes less than a predetermined number of events prior to detection. Other examples of over-sensing or under-sensing criteria are taught in U.S. Pat. No. 7,894,883 to Gunderson et al., incorporated herein by reference in its entirety. If an episode is found to be either not spontaneous or not include regular sensing, the episode is classified as unknown or VOS for the FF EGM channel (132). The episode may be classified as VOS when over-sensing is found.

In response to a determination that the episode received from IMD 16 is spontaneous and includes regular sensing, episode classifier 318 determines the A/V ratio during the beats preceding detection (134). The ratio of atrial sensed events to ventricular sensed events is determined for a predetermined window of sensed events occurring prior to detection by IMD 16 of the cardiac event. In some examples, the predetermined window used for calculating the A/V ratio may be defined by the last 12 ventricular sensed events occurring just prior to the point of detection of the cardiac episode. It is understood that the window may be defined by any predetermined number of ventricular sensed events prior to detection. The number of atrial sensed events occurring within the window is then determined and used to determine the A/V ratio. If the number of atrial sensed events occurring during the window is equal to the number of ventricular sensed events, a determination is made as to whether the atrial sensed events are evenly distributed with the ventricular sensed events, that is, whether there is a 1:1 distribution prior to detection (136). If there is one atrial sensed event located between each adjacent pairs of all of the ventricular sensed events, the event is identified as being a supraventricular tachycardia (SVT) episode (158) for the FF EGM Channel. The rationale behind this classification is that a ventricular arrhythmia would have a shorter ventricular cycle length than the atrial cycle length at some point in the episode.

If the atrial sensed events are determined to be not evenly distributed with the ventricular sensed events in a one to one distribution (136), the classification of the episode is further evaluated. Episode classifier 318 may determine which chamber is leading (138). Episode classifier 318 determines whether the heart rhythm was initiated by conduction in the ventricle or in the atria. In some examples, an onset threshold is determined. Once the onset threshold has been determined, a spatial reference point is identified and used to form a window for determining whether conduction of the heart rhythm was imitated by one of the atrial and the ventricular chambers. For example, an RR interval associated with pre-NID or sinus rhythm, i.e., greater than the onset threshold, occurring prior to an interval correspond to when the episode was detected, may be used as the spatial reference point for forming the window. In some examples, the spatial reference point may be identified by determining by working backwards from the detection until a predetermined number of sequential adjacent intervals occurring prior to the interval associated with the detection is greater than the onset threshold. Other examples of determining a spatial reference point and window for determining which chamber is leading may be found in U.S. Pat. No. 7,894,883 to Gunderson et al., incorporated herein by reference in its entirety.

Determining which chamber is leading (138) may include identification of a spatial reference point, as wells as a predetermined number of intervals centered around the determined spatial reference point. The number of sensed atrial events occurring between each interval within the window is determined. If there is one atrial sensed event between each of the adjacent ventricular sensed vents in the window, the atrium is determined to be initiating conduction. In response to a determination that the atrium is leading, episode classifier 318 classifies the episode as SVT for the FF EGM channel (158). If there is one atrial sensed event between adjacent ventricular sensed events for all except one of the ventricular sensed event intervals, and no atrial sensed events between one set of adjacent ventricular sensed events, then the ventricles are determined to be initiating conduction. If the ventricles are found to be leading, episode classifier 318 classifies the episode as a ventricular tachycardia/ventricular fibrillation (VT/VF) episode (156). If there is one atrial sensed event between each of the adjacent ventricular sensed events for less than the number of intervals minus one, and no atrial sensed event between adjacent ventricular sensed events for more than one of the intervals, then neither the atrium nor the ventricles are determined to be driving conduction. If no determination is made, then processor 86 continues to attempt to classify the episode based on whether the effects the effects of anti-tachycardia pacing (ATP) are indicative of a supraventricular tachycardia episode.

Episode classifier 318 may determine whether the cycle length between atrial events, that is, the interval between P-waves is the same during the episode being classified as during an antitachycardia pacing regimen previously applied to the patient (140). In some examples, a determination about the effects of anti-tachycardia pacing is made using a method of dynamic discrimination described in commonly assigned U.S. Pat. No. 7,317,942, issued Jan. 8, 2008, entitled "DYNAMIC DISCRIMINATION UTILIZING ANTI-TACHY PACING THERAPY IN AN IMPLANTABLE MEDICAL DEVICE" to Brown et al., and incorporated herein by reference in its entirety. For example, instances where IMD 16 delivered an antitachycardia pacing regimen may be identified by IMD 16 or programmer 24 and the corresponding EGM signal data may be stored in memory 92. The EGM signal associated with the therapy may be reviewed to determine a mean cycle length between atrial events occurring prior to the delivery of the antitachycardia pacing therapy and comparing the determined atrial cycle length during the delivery of the pacing therapy to a mean cycle atrial cycle length during the episode. If the difference between the mean atrial cycle and the atrial cycle length during the delivery of the pacing therapy is less than or equal to a predetermined atrial cycle length threshold, such as 30 ms for example, the episode is classified as being a SVT on the FF channel (158). If the difference between the mean atrial cycle length for the episode and the atrial cycle length during the delivery of the pacing therapy is greater than the predetermined threshold then the processor continues with the classification algorithm for the FF EGM channel.

If the PP interval (or atrial cycle) of the episode is not the same as the atrial cycle length during ATP, then the morphology of a maximum interval within the episode being classified and the minimum interval within the episode being classified are compared. Processor 86 determine whether the intervals have the same morphology despite having different RR interval lengths (150). In some examples, the comparison occurs if the difference between the maximum interval and the minimum interval is greater than a predetermined threshold. A determination is then made as to whether the correlation between the morphologies of the two intervals is greater than a predetermined correlation threshold, such as 0.94, for example.

If the correlation between the two intervals is greater than the predetermined correlation threshold, then the detected episode is classified as being SVT for the FF EGM channel (158). If the correlation is below the predetermined correlation threshold, or the difference between the maximum and minimum intervals is below the predetermined threshold for difference between the two intervals, then the morphology of the intervals within the episode are compared to a FF VT template. Episode classifier 318 determines how many of the intervals have a morphology that matches the FF VT template (152). The FF VT template may be one of more FF VT templates stored within memory 92. In some examples the VT template may have been stored during the classification of a previous episode from the same patient. Episode classifier 318 compares each interval within the episode with the FF VT template and determines whether each interval correlates to the FF VT template based on a predetermined correlation threshold. If the number of intervals having morphologies that correlate to the FF VT template is above a predetermined matching percentage threshold, then the morphology for the episode is determined to match the template. In response, the episode is classified at VT/VF for the FF EGM channel (156). If the number of intervals having morphologies that correlate to the FF VT template is below the predetermined matching percentage threshold, then the episode is classified as unknown for the FF EGM channel (133). The matching percentage threshold may be programmable by a default, or may be adjusted by the clinician or other user. In some examples the threshold may be adjusted on a patient-by-patient or clinic-by clinic basis. In some examples, the matching percentage threshold may be approximately between 70% and 85%. In some examples, the matching percentage may be approximately 80%.

If the A/V ratio during the beats preceding detection (134) is such that the number of atrial sensed events is below the number of ventricular sensed events within a window preceding detection, then an interval may be stored as a FF VT template (142). The episode is classified as VT/VF for the FF EGM channel (156). In some examples, the difference between the number of atrial sensed events and the number of ventricular sensed events must be greater than 1.

In response to an A/V ratio during the beats preceding a detection (134) where the number of atrial sensed events is greater than the number of ventricular sensed events, episode classifier 318 determines whether the data used by IMD 16 during the initial classification of the episode as a detected episode includes RR intervals that are regular, and whether the PR intervals are stable (146). In an example to illustrate how episode classifier 318 determines whether the RR intervals are regular and whether the PR intervals are stable (146), an episode being processed includes a number of intervals to detection (NID) of 16 intervals. That is, during the initial detection process IMD 16 detected the occurrence of a cardiac episode once the detection criteria had been met, i.e., once 16 intervals having a rate than the threshold rate were detected. In some examples, IMD 16 continuously stores a buffer containing a number of the most recent intervals of the EGM signal. This may allow IMD 16 to store an EGM signal including all 16 intervals resulting in detection to memory 72 after detection. In order to determine whether the data used by IMD 16 during the initial classification of the episode a detected episode includes intervals that are regular, a modesom of the 16 RR intervals resulting in detection is generated by determining whether the number of intervals in the two highest modes (i.e., most frequent bins) is greater than a predetermined percentage of the number of RR intervals. The percentage may be 67%, for example. If the number of intervals in the two highest modes is above the percentage threshold, then the data is considered to include regular RR intervals.

Episode classifier 318 also determines whether the AV intervals associated with the initial identification of the episode as a cardiac episode are stable. For example, in order to determine whether the AV intervals associate with the initial identification of the episode as a cardiac episode are stable, PR intervals, i.e., the time between an atrial sensed event and a subsequent ventricular sensed event, are determined for each of the 16 intervals. In some examples, in order to reduce the effect of outliers, once the PR intervals are determined for each of the intervals associated with the initial identification of the episode as a cardiac episode, a predetermined number of maximum PR intervals and minimum PR intervals are removed. For example, one sixth of the maximum PR intervals and one sixth of the minimum PR intervals may be removed. A PR range is then determined as the difference between the minimum PR interval and the maximum PR interval. Episode classifier 318 then determines whether the range of PR intervals satisfies a PR stable criterion. For example, a determination may be made as to whether the range of the remaining PR intervals is less than 20 ms. In response to a determination that the RR intervals are regular and the PR intervals are stable, the episode is classified as SVT for the FF EGM channel (158). If episode does not include both regular RR intervals and stable PR intervals, then episode classifier 318 determiners how many atrial events are unassociated with a ventricular event and how many atrial events are associated with a ventricular event (120). The episode classifier 318 may look for approximately consistent AV intervals for atrial events associated with a ventricular event. If the number of atrial events part of an AV interval is above a predetermine threshold, then the cardiac episode is classified as SVT for the NF EGM channel (158) by episode classifier 318.

If the number of unassociated atrial events is below a predetermined threshold, then, as discussed above, the data associated with the episode is examined to determine whether RR intervals with different lengths have approximately the same morphology (150). In some examples the maximum and minimum intervals in the episode are compared and, if the difference in interval value is greater than a predetermined threshold, such as 100 ms for example, then the morphology of the maximum interval is compared to the morphology of the minimum interval. If the morphologies are found to correlate, the episode is classified as SVT for the FF EGM channel (158). As described above, if the maximum and minimum intervals are not found to correlate, then the morphologies of each of the intervals associated with detection of a cardiac episode are compared with a template or templates stored in memory 92, the template or templates being FF VT templates. Episode classifier 318 determines for each of the intervals whether the correlation of the morphology between the interval and the template is greater than a predetermined correlation threshold. If the number of intervals having morphologies that correlate to the stored template is greater than a predetermined matching percentage threshold, then the episodes is classified as being VT/VF for the FF EGM channel (156). If the number of intervals that match is below the matching percentage threshold, then the episode is classified as unknown for the FF EGM channel (132).

FIG. 6C illustrates an example algorithm for determining a final classification for an episode detected by IMD 16 that in some examples is based on both an NF classification and a FF classification. Processor 86 retrieves the results for FF EGM classification (160) and the result from NF EGM classification (162) from memory 92. Episode classifier 318 determines whether the result from one of the channels is VOS (161). In some examples where f either the NF channel EGM or the FF channel EGM has been classified as VOS the final classification is VOS (163) Episode classifier 318 determines if both the results are unknown (164). If both results are unknown, then the final classification is unknown (166). Episode classifier 318 then determines if the NF EGM result is "unknown" (168). If the NF EGM result is unknown, then the final classification is the FF EGM result (170). If the NF EGM result is not unknown, then processor 86 determines if the FF EGM result is "unknown" (172). If the FF EGM result is not unknown, then the final classification is the FF EGM result (170). If the FF EGM result is unknown, then the final classification if the NF EGM result (174). The use of both NF and FF channels results in more of the detected episodes evaluated by processor 86 being classified as either VT/VF or SVT. In turn, the increase in "known" classifications results in greater understanding of how well IMD 16 is performing.

Figure 7:
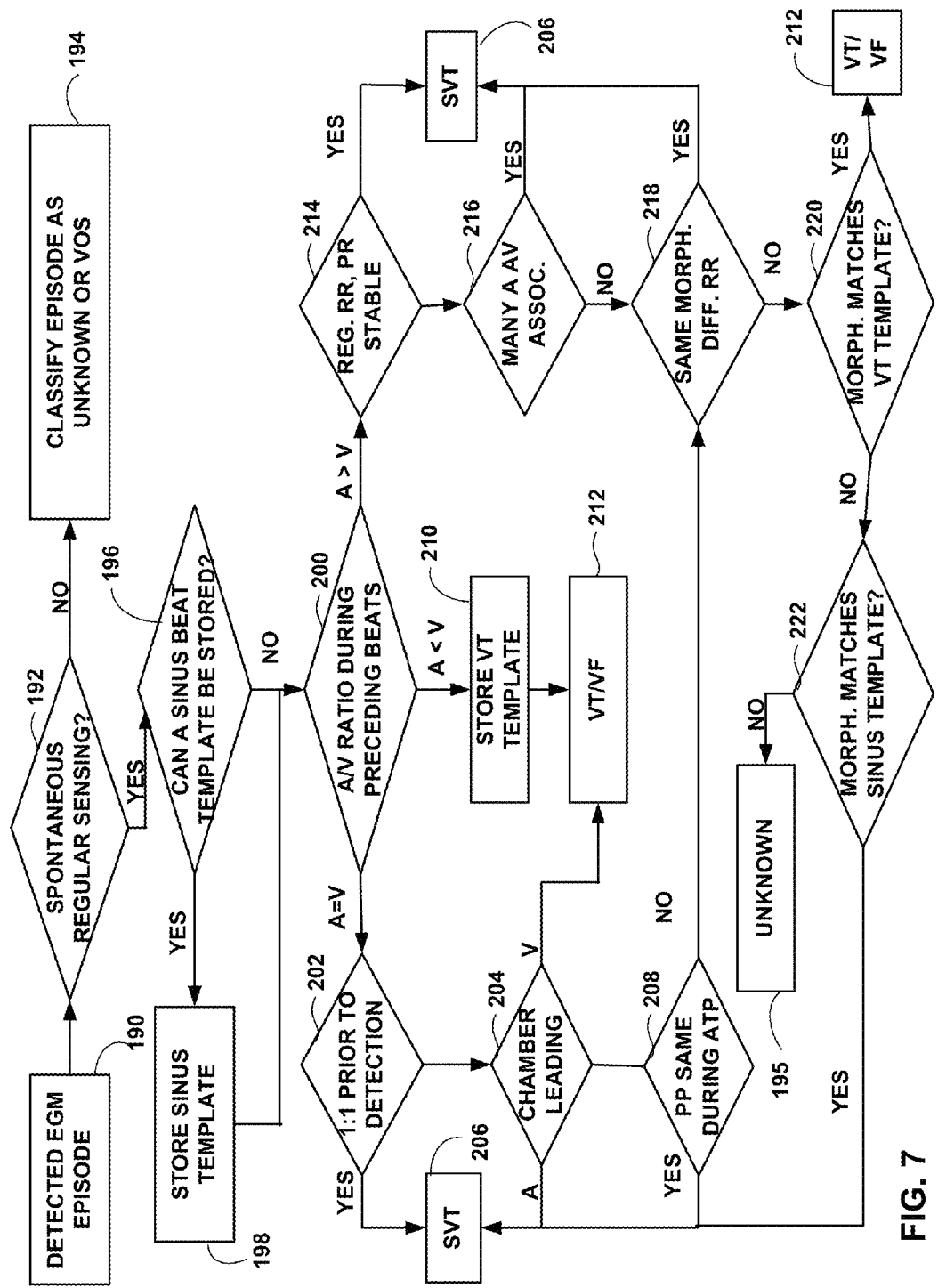
FIG. 7 is a flow chart illustrating an example method of determining a classification for an episode using a sinus rhythm template.

FIG. 7 is a flow chart illustrating an episode classification algorithm that classifies an episode based on EGM signal data associated with an episode detected by IMD 16. The example in FIG. 7, the episode classification algorithm is presented without regard to a NF or FF channel. However, one of skill in the art would understand that the episode classification algorithm shown in FIG. 7, and in particular the use of a sinus beat template, may be used with the classification algorithm of FIG. 6A-6C.

Episode classifier 318 selects a detected EGM episode (100) from stored episodes 94. Episode classifier 318 determines whether the EGM data received from IMD 16 includes spontaneous and regular sensing (192), i.e., not induced. In some examples, a method of determining whether data previously utilized by a device to identify a cardiac episode correspond to regular sensing of events includes a determination as to whether over-sensing or under-sensing has occurred. The determination of over-sensing or under-sensing may be based on a determination of whether one of a predetermined number of over-sensing or under-sensing criteria has been met. An example of an over-sensing criterion includes the existence of simultaneous atrial and ventricular events, except in instances where the ventricular event is ventricular Pace for ATP. An example of an under-sensing criterion includes determining whether at least one sensed AA interval associated with predetermined beats, such as the NID ventricular beats prior to detection of the episode and the atrial interval immediately subsequent to the detection of the episode is greater than a predetermined interval, such as 2500 ms, for example. Another example of under-sensing criteria include determining whether the atrial channel includes less than a predetermined number of events prior to detection. Other examples of over-sensing or under-sensing criteria are taught in U.S. Pat. No. 7,894,883 to Gunderson et al., incorporated herein by reference in its entirety. If an episode is found to be either not spontaneous or not include regular sensing, the episode is classified as unknown or VOS (194). The episode may be classified as VOS if episode classifier 318 determines that over-sensing is present.

In response to a determination that the episode received from IMD 16 is spontaneous and includes regular sensing, Episode classifier 318 determines if one or more sinus beat templates may be stored (196). In determining whether an episode includes and appropriate sinus beat for use as a template, episode classifier 318 determines whether several factors are present in the EGM signal. As described in more detail below with respect to FIGS. 10 and 11, episode classifier 318 determines whether the A to V ratio is 1:1. As discussed above, in order for an episode to have a 1:1 distribution, there needs to be the same number of atrial events and ventricular events, and the events must alternate. Episode classifier 318 then looks for a portion of the episode include a PR interval greater than a first predetermined threshold. In some examples, the first predetermined is approximately 80 ms. Episode classifier 318 also looks for a portion of the episode that includes an RR interval greater than a second predetermined threshold. In some examples, the second predetermined threshold is approximately 500 ms. Episode classifier 318 also looks for a portion of the episode that includes two consecutive RR interval values within less than a third predetermined threshold of each other. In some examples, the third predetermined threshold may be approximately 50 ms. For example, as shown in FIG. 12, the RR intervals leading to selection are 730 ms and 750 ms. If an interval is found to fulfill the requirements than a sinus template may be stored (198) in memory 92. In some examples a sinus template may be selected from an episode that has been classified by IMD 16 or programmer 24 as SVT. Processor 86 selects one of the pre-detection ventricular beats and stores the beat as a sinus template. In some examples, processor 86 may store additional templates for different channels that correspond to the beat selected. The additional templates may be stored to correspond to different electrode configurations. In some examples, multiple sinus template may be stored over time to correspond to multiple different electrode configurations.

Episode classifier 318 determines the A/V ratio of the beats preceding detection (200). The ratio of atrial sensed events to ventricular sensed events is determined for a predetermined window of sensed events occurring prior to detection by IMD 16 of the cardiac episode. In some examples, the predetermined window used for calculating the A/V ratio may be defined by the last 12 ventricular sensed events occurring just prior to the point of detection of the cardiac episode. It is understood that the window may be defined by any predetermined number of ventricular sensed events prior to detection. The number of atrial sensed events occurring within the window is then determined and used to determine the A/V ratio. If the number of atrial sensed events occurring during the window is equal to the number of ventricular sensed events, a determination is made as to whether the atrial sensed events are evenly distributed with the ventricular sensed events, that is, whether there is a 1:1 distribution prior to detection (202). If there is one atrial sensed event located between each adjacent pairs of all of the ventricular sensed events, the episode is identified as being a supraventricular tachycardia (SVT) episode (206). The rationale behind this classification is that a ventricular arrhythmia would have a shorter ventricular cycle length than the atrial cycle length at some point in the episode.

If the atrial sensed events are determined to be not evenly distributed with the ventricular sensed events in a one to one distribution (202) the classification of the episode is further evaluated. Episode classifier 318 may determine which chamber is leading (204). Episode classifier 318 determines whether the heart rhythm was initiated by conduction in the ventricle or in the atria. In some examples, an onset threshold is determined. Once the onset threshold has been determined, a spatial reference point is identified and used to form a window for determining whether conduction of the heart rhythm was imitated by one of the atrial and the ventricular chambers. For example, an RR interval associated with pre-NID or sinus rhythm, i.e., greater than the onset threshold, occurring prior to an interval correspond to when the episode was detected, may be used as the spatial reference point for forming the window. In some examples, the spatial reference point may be identified by determining by working backwards from the detection until a predetermined number of sequential adjacent intervals occurring prior to the interval associated with the detection is greater than the onset threshold. Other examples of determining a spatial reference point and window for determining which chamber is leading may be found in U.S. Pat. No. 7,894,883 to Gunderson et al., incorporated herein by reference in its entirety.

Determining which chamber is leading (204) may include identifying a spatial reference point, as wells as a predetermined number of intervals centered around the determined spatial reference point. Episode classifier 218 determines the number of sensed atrial events occurring between each interval within the window. If there is one atrial sensed event between each of the adjacent ventricular sensed vents in the window, episode classifier 318 determines that the atrium is initiating conduction. In response to a determination that the atrium is leading, episode classifier 318 classifies the episode as SVT (206). If there is one atrial sensed event between adjacent ventricular sensed events for all except one of the ventricular sensed event intervals, and no atrial sensed events between one set of adjacent ventricular sensed events, then episode classifier 318 determines that the ventricles are initiating conduction. If the ventricles are found to be leading, episode classifier 318 classifies the episode as a ventricular tachycardia/ventricular fibrillation (VT/VF) episode (212). If there is one atrial sensed event between each of the adjacent ventricular sensed events for less than the number of intervals minus one, and no atrial sensed event between adjacent ventricular sensed events for more than one of the intervals, then neither the atrium nor the ventricles are determined to be driving conduction. If no determination is made, then episode classifier 318 continues to attempt to classify the episode based on whether the effects the effects of anti-tachycardia pacing (ATP) are indicative of a supraventricular tachycardia episode.

Episode classifier 318 may determine whether the cycle length between atrial events, that is, the interval between P-waves is the same during the episode being classified as during an antitachycardia pacing regimen previously applied to the patient (208). In some examples, a determination about the effects of anti-tachycardia pacing is made using a method of dynamic discrimination described in commonly assigned U.S. Pat. No. 7,317,942, issued Jan. 8, 2008, entitled "DYNAMIC DISCRIMINATION UTILIZING ANTI-TACHY PACING THERAPY IN AN IMPLANTABLE MEDICAL DEVICE" to Brown et al., and incorporated herein by reference in its entirety. For example, instances where IMD 16 delivered an antitachycardia pacing regimen may be identified by IMD 16 or programmer 24 and the corresponding EGM signal data may be stored in memory 92. The EGM signal associated with the therapy may be reviewed to determine a mean cycle length between atrial events occurring prior to the delivery of the antitachycardia pacing therapy and comparing the determined atrial cycle length during the delivery of the pacing therapy to a mean cycle atrial cycle length during the episode. If the difference between the mean atrial cycle and the atrial cycle length during the delivery of the pacing therapy is less than or equal to a predetermined atrial cycle length threshold, such as 30 ms for example, the episode is classified as being a SVT (206). If the difference between the mean atrial cycle length for the episode and the atrial cycle length during the delivery of the pacing therapy is greater than the predetermined threshold then episode classifier 318 continues with the classification algorithm.

If the PP interval (or atrial cycle) of the episode is not the same as the atrial cycle length during ATP, then the morphology of a maximum interval within the episode being classified and the minimum interval within the episode being classified are compared. Episode classifier 318 determines whether the intervals have the same morphology despite having different RR interval lengths (218). In some examples, the comparison occurs if the difference between the maximum interval and the minimum interval is greater than a predetermined threshold. A determination is then made as to whether the correlation between the morphologies of the two intervals is greater than a predetermined correlation threshold, such as 0.94, for example.

If the correlation between the two intervals is greater than the predetermined correlation threshold, then the detected episode is classified as being SVT (206). If the correlation is below the predetermined correlation threshold, or the difference between the maximum and minimum intervals is below the predetermined threshold for difference between the two intervals, then the morphology of the intervals within the episode are compared to a VT template. Episode classifier 318 determines how many of the intervals have a morphology that matches the VT template (220). The VT template may be one of more VT templates stored within memory 92. In some examples the VT template may have been stored during the classification of a previous episode from the same patient. Episode classifier 318 compares each interval within the episode with the VT template and determines whether each interval correlates to the VT template based on a predetermined correlation threshold. If the number of intervals having morphologies that correlate to the VT template is above a predetermined matching percentage threshold, then the morphology for the episode is determined to match the template. In response, the episode is classified at VT/VF (212). If the number of intervals having morphologies that correlate to the VT template is below the predetermined matching percentage threshold, then the episode is classified as unknown (195). The matching percentage threshold may be programmable by a default, or may be adjusted by the clinician or other user. In some examples the threshold may be adjusted on a patient-by-patient or clinic-by clinic basis. In some examples, the matching percentage threshold may be between approximately 70% and 85%. In some examples, the matching percentage may be approximately 80%.

In the episode that the A/V ratio during the beats preceding detection (196) is such that the number of atrial sensed events is below the number of ventricular sensed events within a window preceding detection, then an interval may be stored as a VT template (210). The episode is classified as VT/VF (212). In some examples, the difference between the number of atrial sensed events and the number of ventricular sensed events must be greater than 1.

In response to an A/V ratio during the beats preceding a detection (200) where the number of atrial sensed events is greater than the number of ventricular sensed events, episode classifier 318 determines whether the data used by IMD 16 during the initial classification of the episode includes RR intervals that are regular, and whether the PR intervals are stable (214). In an example to illustrate how processor 86 determines whether the RR intervals are regular and whether the PR intervals are stable (214), an episode being processed includes a number of intervals to detection (NID) of 16 intervals. That is, during the initial detection process IMD 16 detected the occurrence of a cardiac episode once the detection criteria had been met, i.e., once 16 intervals having a rate lower than the threshold rate were detected. In some examples, IMD 16 continuously stores a buffer containing a number of the most recent intervals of the EGM signal. This may allow IMD to store an EGM signal including all 16 intervals resulting in detection to memory 72 after detection. In order to determine whether the data used by IMD 16 during the initial classification of the episode as a detected episode includes intervals that are regular a modesum of the 16 RR intervals resulting in detection is generated by determining whether the number of intervals in the two highest modes (i.e., most frequent bins) is greater than a predetermined percentage of the number of RR intervals. The percentage may be 67%, for example. If the number of intervals in the two highest modes is above the percentage threshold, then the data is considered to include regular RR intervals.

Episode classifier 318 also determines whether the AV intervals associated with the initial identification of the episode as a cardiac episode are stable. For example, in order to determine whether the AV intervals associate with the initial identification of the episode as a cardiac episode are stable, PR intervals, i.e., the time between an atrial sensed event and a subsequent ventricular sensed event, are determined for each of the 16 intervals. In some examples, in order to reduce the effect of outliers, once the PR intervals are determined for each of the intervals associated with the initial identification of the episode as a cardiac episode, a predetermined number of maximum PR intervals and minimum PR intervals are removed. For example, one-sixth of the maximum PR intervals and one sixth of the minimum PR intervals may be removed. A PR range is then determined as the difference between the minimum PR interval and the maximum PR interval. Episode classifier 318 then determines whether the range of PR intervals satisfies a PR stable criterion. For example, a determination may be made as to whether the range of the remaining PR intervals is less than 20 ms. In response to a determination that the RR intervals are regular and the PR intervals are stable, the episode is classified as SVT (206). If episode does not include both regular RR intervals and stable PR intervals then episode classifier 318 determiners how many atrial sensed events are unassociated with a ventricular sensed event and how many atrial events are associated with a ventricular event (120). The episode classifier 318 may look for approximately consistent AV intervals for atrial sensed events associated with a ventricular sensed event. If the number of atrial sensed events part of an AV interval is above a predetermine threshold, then the cardiac episode is classified as SVT for the NF EGM channel (158) by episode classifier 318.

If the number of unassociated atrial events is below a predetermined threshold, as discussed above, the data associated with the episode is examined to determine whether RR intervals with different lengths have approximately the same morphology (218). In some examples the maximum and minimum intervals in the episode are compared and, if the difference in interval value is greater than a predetermined threshold, such as 100 ms for example, then the morphology of the maximum interval is compared to the morphology of the minimum interval. If the morphologies are found to correlate, the episode is classified as SVT (206). As described above, if the maximum and minimum intervals are not found to correlate, then the morphologies of each of the intervals associated with detection of a cardiac episode are compared with a template or templates stored in memory 92, the template or templates being VT templates. Episode classifier 318 determines for each of the intervals whether the correlation of the morphology between the interval and the template is greater than a predetermined correlation threshold. If then number of intervals having morphologies that correlate to the stored template is greater than a predetermined matching percentage threshold, than the episodes is classified as being VT/VF (220). If the number of intervals that match is below the matching percentage threshold, then episode classifier 318 determines if the morphology of the intervals matches a sinus template (222).

Determining whether the morphology of the episode matches a sinus template (222) is performed in a manner similar to the one used to determine if the morphology of the episode matches a VT template (220). The morphologies of each of the intervals within the episode are compared with a sinus template or templates stored in memory 92. A particular sinus template may be selected based on, for example, the most common morphology at time of possible collection of a template, or waveform average. In some examples, a particular sinus template may be selected based on the channel of the EGM signal being analyzed. Episode classifier 318 determines for each of the intervals whether the correlation between the morphologies of the interval and the sinus template is greater than a predetermined correlation threshold. If the number of intervals having morphologies that correlate to the stored template is greater than a predetermined matching percentage threshold, then the episode is classified as SVT (206). If the number of intervals that match is below the matching percentage threshold, then the episode is classified as unknown (194).

Figure 8:
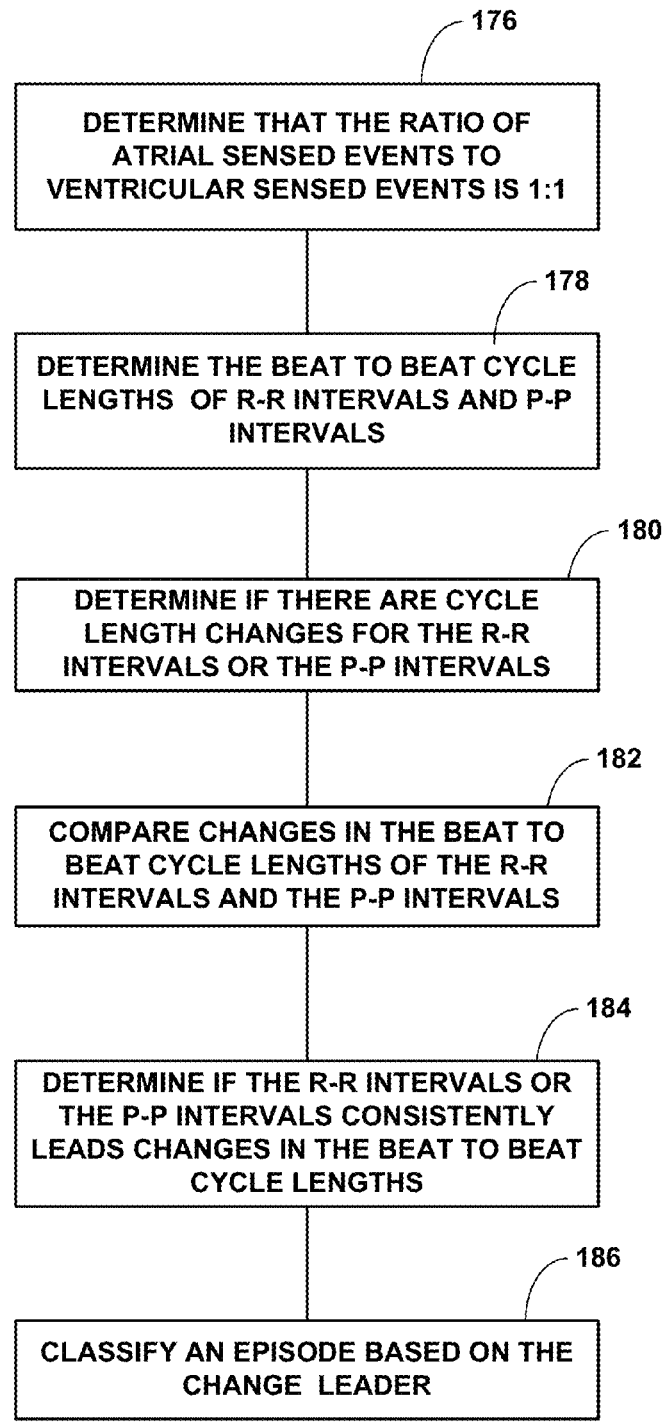
FIG. 8 is a flow chart illustrating an example method of classifying an episode when the ratio of atrial sensed events and ventricular sensed events is 1:1.

FIG. 8 is flow chart illustrating a method of classifying an episode when the ratio of atrial sensed event and ventricular sensed event is 1:1. The method may be used with algorithm illustrated in FIGS. 6A-6C or the algorithm in FIG. 7. The method may also be used for real time classification of an EGM signal by IMD 16. As discussed above with respect to FIGS. 6A, 6B and 7, in order to determine that the ratio of atrial sensed events to ventricular sensed events is 1:1 (176) episode classifier 318 determines if each of the adjacent ventricular sensed events is separated by a single atrial sensed event. When used as part of a larger classification scheme, if there is not a 1:1 ratio between atrial sensed events and ventricular sensed events, episode classifier 318 may move to the next step in the classification algorithm. If the atrial sensed events and ventricular sensed events are appropriately interleaved, then episode classifier 318 determines the beat to beat cycle lengths of RR intervals and PP intervals (178). Using the determined cycle lengths, processor 86 determines if there are cycle length changes for the RR intervals or the PP intervals (180). In some examples, consecutive intervals, either RR intervals or PP intervals, are not classified as having a change in cycle length if the variation in the interval length is less than a predetermined threshold. In some examples, the predetermined threshold may be 10% of the previous cycle length. The use of a threshold removes minor fluctuations in the cycle length. In some examples, episode classifier 318 determines the direction of the change in interval length.

Episode classifier 318 compares changes in the beat to beat cycle lengths of the RR intervals and the PP intervals (182). The processor compares changes in RR intervals to any changes in PP intervals, and vice versa, for intervals in approximately the same time period. For a given comparison processor 86 may determine which interval changed first and whether the interval lengths changed in the same direction, i.e., both increasing or both decreasing. Episode classifier 318 then determines if the RR intervals or the PP intervals consistently leads changes in the beat to beat cycle lengths (184). The episode is then classified based on the change leader (186). If the atrial sensed events and corresponding PP intervals lead changes in interval length then the episode is classified as SVT. If the ventricular sensed events and corresponding RR intervals lead the changes in interval length then the episode is classified as VT/VF. If there are no changes in interval length or there is not a consistent leader to the changes in interval length, then the episode is not classified.

Figure 9A:
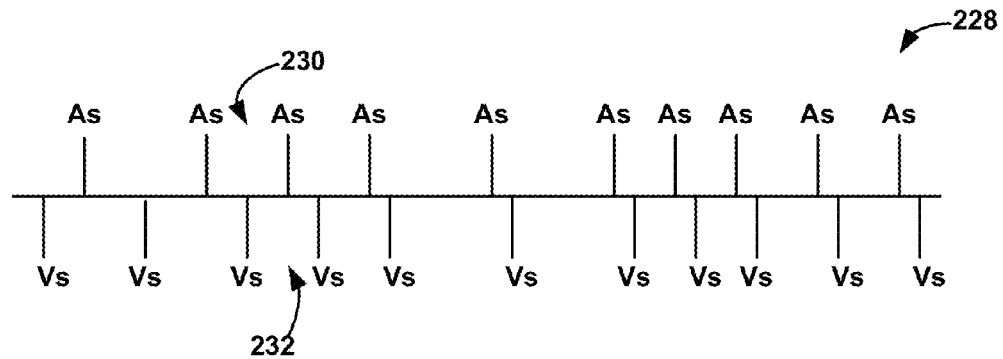
FIG. 9A is an example marker channel having a 1:1 ratio.

FIG. 9A is an example marker channel 228 having a 1:1 ratio. As shown in FIG. 9A, each ventricular sensed event $V_s$ is separated by an atrial sensed event $A_s$. In marker channel 228 changes in the interval length between the atrial sensed events consistently lead the changes in the interval length between ventricular sensed events. For example, PP interval 230 is shorter than preceding PP interval. RR interval 232 is also shorter than the preceding RR interval. Because interval 230 starts before interval 232, interval 230 is considered to be leading the change in interval length. Throughout the portion of marker channel 228 depicted the length of time between atrial sensed events changes before the length of time between ventricular sensed events changes. Using the method described in FIG. 8, an episode including marker channel 228 would be classified as SVT.

Figure 9B:
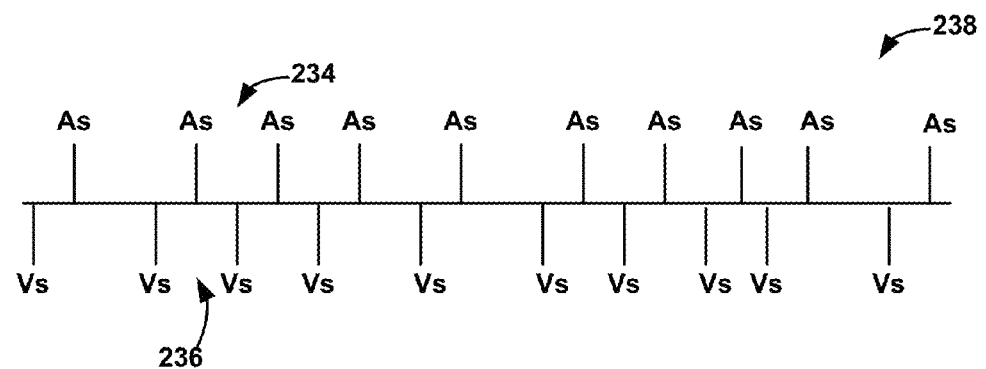
FIG. 9B is an example marker channel having a 1:1: ratio.

FIG. 9B is an example marker channel 238 having a 1:1 ratio. As shown in FIG. 9B, each ventricular sensed event $V_s$ is separated by an atrial sensed event $A_s$. In marker channel 238 changes in the interval length between the ventricular sensed events consistently lead the changes in the interval length between atrial sensed events. For example, RR interval 236 is shorter than the preceding RR interval. PP interval 234 is also shorter than the preceding PP interval. Because interval 236 starts before interval before interval 234, interval 236 is considered to be leading the change in interval length. Throughout the portion of marker channel 238 depicted the length of time between ventricular sensed events $V_s$ changes before the length of time between atrial sensed events $A_s$. Using the method described in FIG. 8, an episode including marker channel 238 would be classified as VT/VF.

With regards to FIGS. 8, 9A and 9B, if either RR interval or the PP interval consistently leads with respect to beat to beat cycle length changes, then it is most likely contraction is originating in a location corresponding to the respective portion of the EGM signal. A P-wave corresponds to contraction of the atrium. Accordingly, if any changes in cycle length show up in the PP interval first, contraction of the heart is most likely starting in the atrium. Similarly, an R-wave corresponds to contraction in the ventricles. Accordingly, if any changes in cycle length show up in the RR interval first, contraction of the heart is most likely starting in the ventricles. Based on this association one can reasonably assume that if an arrhythmia is occurring that is led by the atrium, it is a supraventricular tachycardia, and if the arrhythmia is led by the ventricles it is either ventricular tachycardia or ventricular fibrillation.

Figure 10:
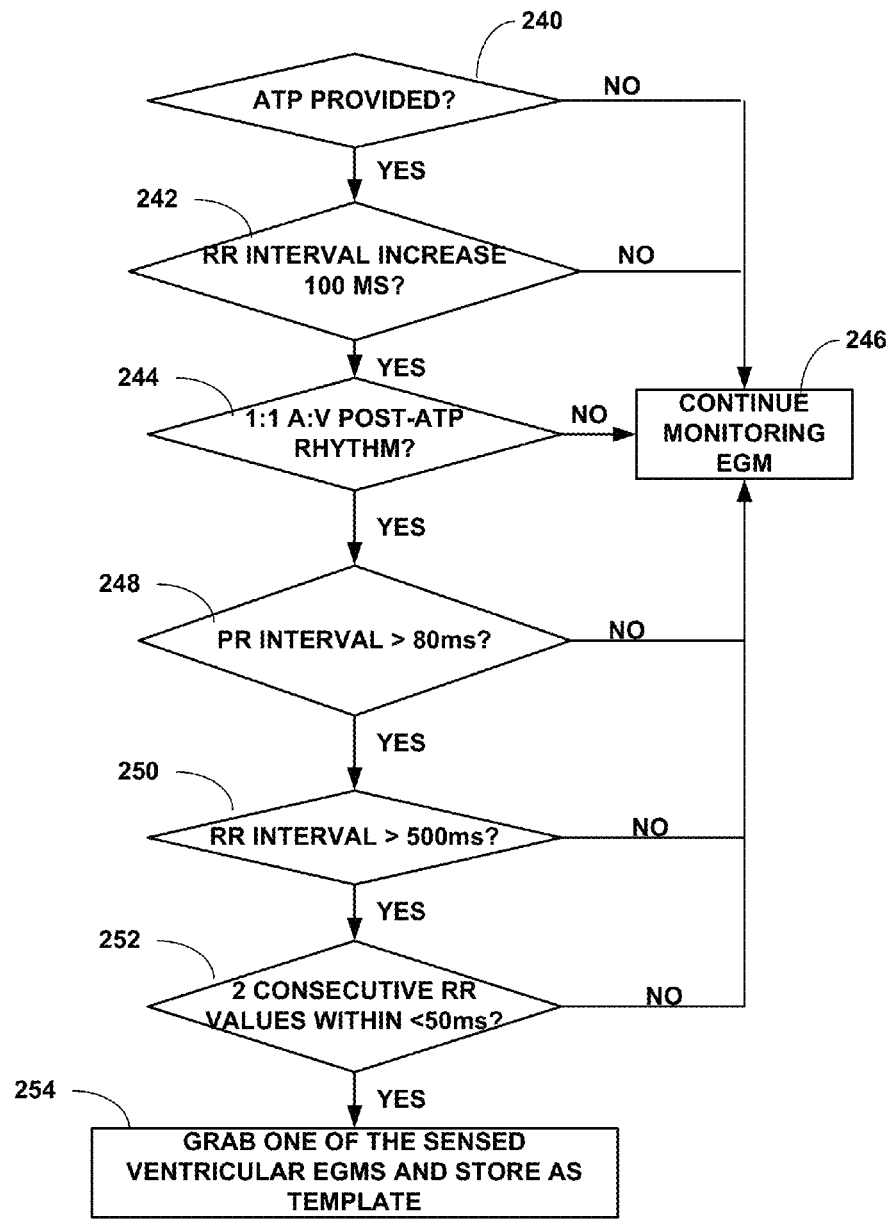
FIG. 10 is an example method for automatically selecting a sinus template after anti-tachycardia pacing (ATP).

FIG. 10 depicts an example method of selecting a sinus template during anti-tachycardia pacing (ATP). The method may be implemented by either IMD 16 or an external device such as programmer 24. A processor, such as processor 70 or processor 86, determines if ATP has been provided 240. If not, then the device continues to monitor the EGM signal (246). IF ATP has been provided (240), then the processor next determines if the RR interval has increased by at least 100 ms (242) from pre diagnosis of arrhythmia and application of ATP to post-ATP. An increase in RR interval by 100 ms or more may indicated that the ATP has been successful. The processor then determines if there is a 1:1 A:V post-ATP rhythm (244). As discussed above a 1:1 AV rhythm comprises a marker channel with alternating atrial sensed events and ventricular sensed events, where there are no occurrences of two of the same time of event in a row. The processor next determines if the PR interval is greater than 80 ms (248). Processor 86 also determines if the post ATP signal include an RR interval greater than 500 ms (250). Processor 86 also determines if there are two consecutive RR interval values within 50 ms (252). The processor 86 selects one of the sensed ventricular EGMs and stores the selected sensed ventricular EGM as a template (254).

A template collected according to the method of FIG. 10 may be used by an external device as part of a classification algorithm. The template may also be used during real time detection by the IMD 16 to strengthen or make a decision regarding diagnosis. For example. If the current heart rate is within the VT/VF zone, then the current morphology is compared to the sinus template. If a match is found, IMD withholds detection of VT/VF. If the two do not match, a normal VT/VF algorithm may continue.

Figure 11:
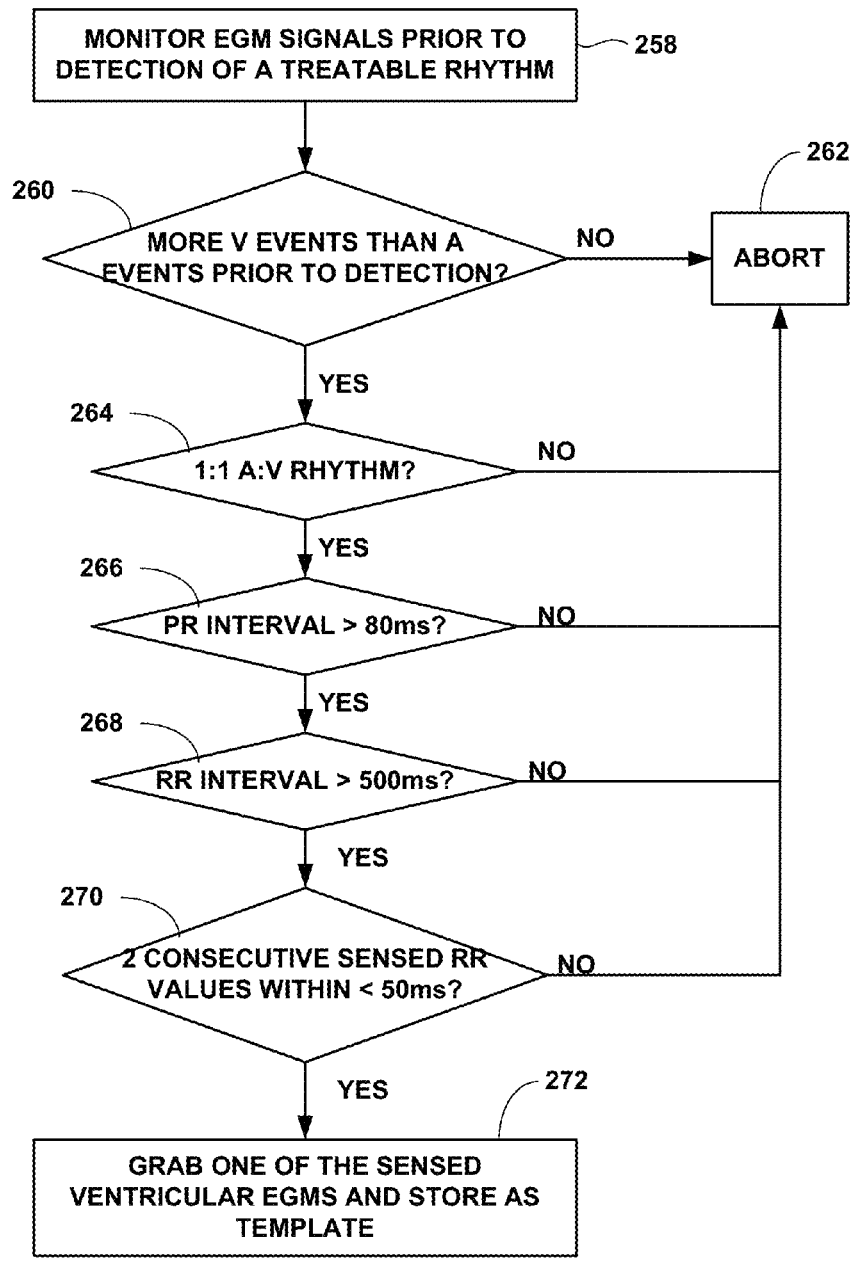
FIG. 11 is an example method for automatically selecting a sinus template from a pre-onset EGM signal.
Figure 12:
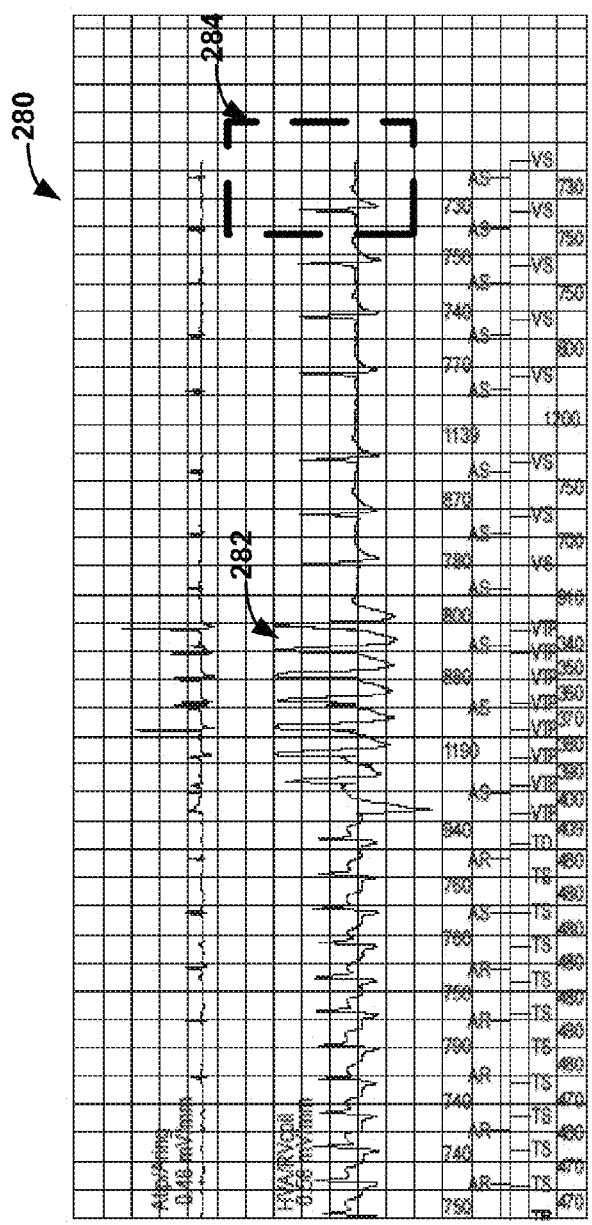
FIG. 12 is an example EGM signal including ATP and a selected sinus template.

FIG. 11 depicts an example method of selecting a sinus template based on an EGM signal prior to diagnosis of a cardiac episode by IMD 16. Episode classifier 318 monitors the EGM signals prior to detection of a treatable rhythm (258) within an episode provided by IMD 16 to programmer 24. Episode classifier 318 determines if there were more ventricular events than atrial events prior to detection (260) and diagnosis. If there are not more ventricular events than atrial events in the episode prior to detection then the attempt to collect a sinus template ends (262). If there are more ventricular sensed events than atrial sensed events, the processor determines if the signal prior to onset includes a portion that has a 1:1 A:V rhythm (264). If there is a portion with a 1:1 A:V rhythm, then processor 86 determines if there is a PR interval that is greater than 80 ms (266) in the portion of the episode with a 1:1 A:V rhythm. The processor also determines if there is an RR interval greater than 500 ms (268). The last requirement for selecting an interval to save as a template is the presence of two consecutive sensed RR intervals values within less than 50 ms of each other (270). If any of the requirements are missing, then the process ends (262) and no template is collected. If all are present, then Episode classifier 318 grabs one of the sensed intervals and stores it as a sinus template (272). The interval selected is one of the ventricular sensed EGM that is close together.

FIG. 12 includes an EGM signal 280 including successful anti-tachycardia pacing 282 and an interval 284 that is appropriately selected as a sinus template. EGM signal fits the criteria as outlined in FIG. 10. An interval 284 is selected and stored separately for use as a sinus template in various classification algorithms.

Figure 13:
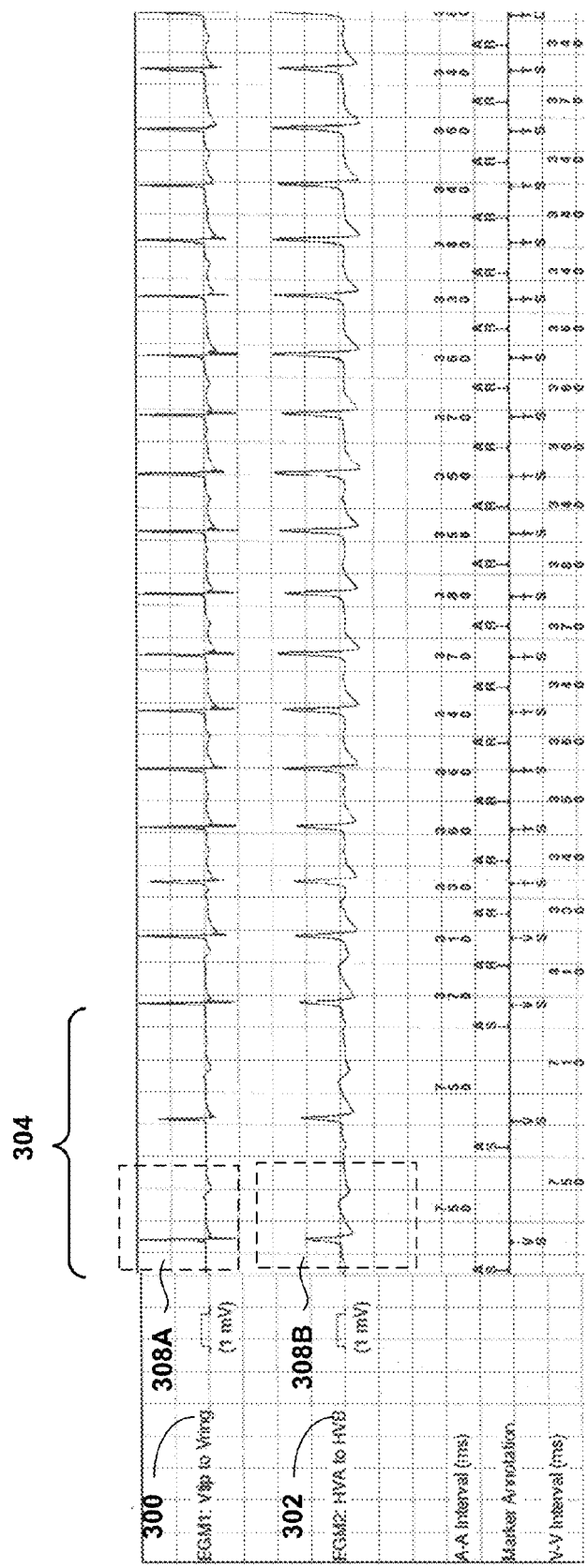
FIG. 13 is an example pre-onset EGM signal including a selected sinus template.

FIG. 13 includes EGM signals 300 and 302 including a pre-onset of episode period 304. As shown in FIG. 13, the portions within the dotted boxes, 308A and 308B, are collected sinus templates for the respective EGM signal channels. The ventricular template may be selected based on the method put forth in FIG. 11.

The techniques described in this disclosure may be implemented, at least in part, in hardware, software, firmware, or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as random access memory (RAM), read-only memory (ROM), non-volatile random access memory (NVRAM), electrically erasable programmable read-only memory (EEPROM), FLASH memory, magnetic media, optical media, or the like. The instructions may be executed to support one or more aspects of the functionality described in this disclosure.

Various embodiments of the invention have been described. These and other embodiments are within the scope of the following claims.

What is claimed is:

1. A method comprising:
    collecting a sinus template from a first ventricular EGM signal,
        wherein the sinus template comprises a portion of the first ventricular EGM signal including at least one ventricular beat, and
        wherein collecting the sinus template comprises collecting the sinus template from a portion of the ventricular EGM that occurred when the ventricular EGM signal and an atrial EGM signal indicated a one to one ratio of atrial events to ventricular events, a P-R interval greater than a first predetermined threshold, an R-R interval greater than a second predetermined threshold, and two consecutive R-R intervals within a predetermined range;
    comparing the sinus template to a second ventricular EGM signal; and
    determining, based on the comparison, whether the morphology of the second ventricular EGM signal matches the sinus template.

2. The method of claim 1, wherein the sinus template comprises a portion of the first ventricular EGM signal adjacent and subsequent to an anti-tachycardia pacing period.

3. The method of claim 2, wherein collecting the sinus template comprises collecting the sinus template when the portion of the first ventricular EGM signal adjacent and subsequent to the anti-tachycardia pacing period comprises an R-R interval that has increased by at least about 100 milliseconds (ms) from a pre anti-tachycardia pacing R-R interval.

4. The method of claim 1, wherein the sinus template comprises a portion of the first ventricular EGM signal prior and adjacent to onset of a cardiac arrhythmia episode.

5. The method of claim 1, further comprising preforming real-time diagnosis of cardiac arrhythmia based on the sinus template by an implantable medical device.

6. The method of claim 1, further including determining whether a cardiac arrhythmia diagnosis previously made by an implantable medical device was correct based on the sinus template.

7. The method of claim 1, further comprising:
    determining whether a morphology of the second ventricular EGM signal and a morphology of the sinus template match; and
    classifying an episode including the second ventricular EGM signal as a supraventricular tachycardia in response to determining that the morphologies match.

8. The method of claim 7, wherein determining whether the morphologies match comprises
    comparing each of a plurality of intervals of the second ventricular EGM signal to the sinus template;
    determining, based on the comparison, a level of correlation between each of the plurality of intervals and the sinus template;
    classifying each of the plurality of intervals as matched or unmatched based on a predetermined threshold for level of correlation;
    comparing a percentage of intervals classified as matched to a predetermined matching percentage threshold, and
    determining that the morphologies match in response to the percentage of intervals classified as matched being above the predetermined matching percentage threshold.

9. The method of claim 1, further comprising comparing an episode comprising the second ventricular EGM signal to a VT template, and:
    in response to a match between the episode and the VT template classifying the episode as ventricular tachycardia or ventricular fibrillation; and
    in response to no match between the episode and the VT template, comparing the episode to the sinus template.

10. The method of claim 1, wherein the first predetermined threshold is about 80 ms, the second predetermined threshold is about 500 ms, and the predetermined range is about 50 ms.

11. A device comprising:
    a processor configured to
        collect a sinus template from a first ventricular EGM signal,
        wherein the sinus template comprises a portion of the first ventricular EGM signal including at least one ventricular beat, and
        wherein collecting the sinus template comprises collecting the sinus template from a portion of the ventricular EGM that occurred when the ventricular EGM signal and an atrial EGM signal indicated a one to one ratio of atrial events to ventricular events, a P-R interval greater than a first predetermined threshold, an R-R interval greater than a second predetermined threshold; and two consecutive R-R intervals within a predetermined range;
        compare the sinus template to a second ventricular EGM signal, and
        determine, based on the comparison, whether the morphology of the second ventricular EGM signal matches the sinus template.

12. The device of claim 11, further including a sensing module configured to receive the EGM signal from electrodes coupled to the device.

13. The device of claim 11, wherein the sinus template comprises a portion of the first ventricular EGM signal adjacent and subsequent to an anti-tachycardia pacing period.

14. The device of claim 13, wherein collecting the sinus template comprises collecting the sinus template when the portion of the first ventricular EGM signal adjacent and subsequent to the anti-tachycardia pacing period comprises an R-R interval that has increased by at least about 100 ms from a pre anti-tachycardia pacing R-R interval.

15. The device of claim 11, wherein the device is an implantable medical device and the processor is further configured to preform real time diagnosis of cardiac arrhythmia based on the sinus template.

16. The device of claim 11, wherein the processor is further configured to determine whether a cardiac arrhythmia diagnosis previously made by the implantable medical device was correct based on the comparison of the second ventricular EGM signal to the sinus template.

17. The device of claim 11, wherein the processor is further configured to
    determine whether a morphology of the second ventricular EGM signal and a morphology of the sinus template match; and
    classify an episode including the second ventricular EGM signal as a supraventricular tachycardia in response to determining that the morphologies match.

18. The device of claim 17, wherein the processor if further configured to make the determination whether the morphologies match by
    comparing each of a plurality of intervals of the second ventricular EGM signal to the sinus template;
    determining, based on the comparison, a level of correlation between each of the plurality of intervals and the sinus template;
    classifying each of the plurality of intervals as matched or unmatched based on a predetermined threshold for level of correlation;
    comparing a percentage of intervals classified as matched to a predetermined matching percentage threshold, and
    determining that the morphologies match in response to the percentage of intervals classified as matched being above the predetermined matching percentage threshold.

19. The device of claim 11, wherein the processor if further configured to compare an episode comprising the second EGM signal to a VT template, and
    in response to a match between the episode and the VT template classify the episode as ventricular tachycardia or ventricular fibrillation; and
    in response to no match between the episode and the VT template, compare the episode to the sinus template.

20. The device of claim 11, wherein the first predetermined threshold is about 80 ms, the second predetermined threshold is about 500 ms, and the predetermined range is about 50 ms.

21. A device comprising:
    means for collecting a sinus template from an EGM signal; the sinus template collected when the EGM signal has a one to one ratio of atrial events to ventricular events, a P-R interval greater than 80 milliseconds (ms), an R-R interval greater than 500 ms; and two consecutive R-R intervals within 50 ms of each other;
    means for comparing the sinus ventricular beat template to a second EGM signal, and
    means for determining, based on the comparison, whether the morphology of the second EGM signal matches the sinus template.

22. A computer-readable medium containing instructions, the instructions causing a programmable processor to:
    collect a sinus template from a first ventricular EGM signal,
    wherein the sinus template comprises a portion of the first ventricular EGM signal including at least one ventricular beat, and
    wherein collecting the sinus template comprises collecting the sinus template from a portion of the ventricular EGM that occurred when the ventricular EGM signal and an atrial EGM signal indicated a one to one ratio of atrial events to ventricular events, a P-R interval greater than a first predetermined threshold, an R-R interval greater than a second predetermined threshold; and two consecutive R-R intervals within a predetermined range;
    compare the sinus template to a second ventricular EGM signal, and
    determine, based on the comparison, whether the morphology of the second ventricular EGM signal matches the sinus template.

* * * * *